(12) United States Patent
Chang et al.

(10) Patent No.: US 12,180,156 B2
(45) Date of Patent: Dec. 31, 2024

(54) DEUTERATED PROTEASE INHIBITORS

(71) Applicants: Kansas State University Research Foundation, Manhttan, KS (US); Wichita State University, Wichita, KS (US); University of Iowa Research Foundation, Iowa City, IA (US)

(72) Inventors: Kyeong-Ok Chang, Manhttan, KS (US); Yunjeong Kim, Manhattan, KS (US); William C. Groutas, Wichita, KS (US); Stanley Perlman, Iowa City, IA (US)

(73) Assignees: Kansas State University Research Foundation, Manhattan, KS (US); Wichita State University, Wichita, KS (US); University of Iowa Research Foundation, Iowa City, IA (US)

( * ) Notice: Subject to any disclaimer, the term of this patent is extended or adjusted under 35 U.S.C. 154(b) by 482 days.

(21) Appl. No.: 17/343,334

(22) Filed: Jun. 9, 2021

(65) Prior Publication Data

US 2021/0380531 A1    Dec. 9, 2021

Related U.S. Application Data

(60) Provisional application No. 63/036,542, filed on Jun. 9, 2020.

(51) Int. Cl.
C07D 207/26    (2006.01)
A61P 31/14    (2006.01)

(52) U.S. Cl.
CPC ............ *C07D 207/26* (2013.01); *A61P 31/14* (2018.01); *C07B 2200/05* (2013.01)

(58) Field of Classification Search
CPC .... C07D 207/26; C07B 2200/05; A61P 31/14
See application file for complete search history.

(56) References Cited

U.S. PATENT DOCUMENTS

| | | |
|---|---|---|
| 9,309,284 B2 | 4/2016 | Chang et al. |
| 9,474,759 B2 | 10/2016 | Chang et al. |
| 10,143,739 B2 | 12/2018 | Chang et al. |
| 11,013,779 B2 | 5/2021 | Chang et al. |
| 11,033,600 B2 | 6/2021 | Chang et al. |
| 2014/0243341 A1 | 8/2014 | Chang et al. |
| 2019/0070184 A1 | 3/2019 | Wang et al. |
| 2019/0151400 A1 | 5/2019 | Chang et al. |
| 2021/0380531 A1 | 12/2021 | Chang et al. |
| 2023/0150933 A1 | 5/2023 | Chang et al. |

FOREIGN PATENT DOCUMENTS

| | | |
|---|---|---|
| WO | 2013166319 | 11/2013 |
| WO | 2017222935 | 12/2017 |
| WO | 2021202460 | 10/2021 |

OTHER PUBLICATIONS

"Deuterium" Encyclopedia Britannica. 2009. Encyclopedia Britannica Online. Feb. 18, 2009 <http://www.britannica.com/EBchecked/topic/159684/deuterium>.*
Browne "Chapter 2. Isotope Effect: Implications for pharmaceutical investigations; Stable isotopes in pharmaceutical research" Elsevier; Amsterdam, 1997.*
Galasiti Kankanamalage et al., J. Med. Chem., 2015, 58, 7, 3144-3155.*
International Search Report and Written Opinion in PCT/US2021/036625, dated Sep. 15, 2021.

* cited by examiner

*Primary Examiner* — Alicia L Otton
(74) *Attorney, Agent, or Firm* — Hovey Williams LLP; Crissa A. Cook

(57) ABSTRACT

Compounds and treatment methods with compounds exhibiting antiviral activity and/or inhibition of viral replication against viruses, particularly those belonging to the picornavirus-like supercluster, including coronavirus having a formula:

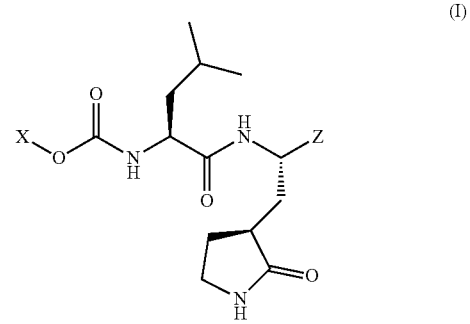

or a prodrug or pharmaceutically-acceptable salt thereof, where:
each X comprises at least one cyclic moiety directly attached to the oxygen or connected via an alkyl linkage, where at least one of the linkage and/or the X moiety comprises a deuterium substitution; and
Z is selected from the group consisting of aldehydes and bisulfite salts, or the ester or carbamate prodrugs thereof.

14 Claims, 6 Drawing Sheets
(5 of 6 Drawing Sheet(s) Filed in Color)

DEUTERATED PROTEASE INHIBITORS

CROSS-REFERENCE TO RELATED APPLICATIONS

The present application claims the priority benefit of U.S. Provisional Patent Application Ser. No. 63/036,542, filed Jun. 9, 2020, entitled DEUTERATED PROTEASE INHIBITORS, incorporated by reference in its entirety herein.

FEDERALLY SPONSORED RESEARCH OR DEVELOPMENT

This invention was made with government support under Contract No. R01AI130092 awarded by National Institutes of Health. The government has certain rights in the invention.

BACKGROUND OF THE INVENTION

Field of the Invention

The present invention relates to improvement of efficacy and pharmacokinetics of protease inhibitors via deuteration.

Description of Related Art

Coronaviruses are a large group of viruses that can cause a wide variety of diseases in humans and animals. They are single-stranded, positive-sense RNA viruses that belong to four genera, designated α, β, γ, and δ coronaviruses, in the Coronaviridae family. Human coronaviruses (229E, NL63, OC43, and HKU1) generally cause mild upper respiratory infections. However, global outbreaks of new human coronavirus infections with severe respiratory disease have periodically emerged from animals, including Severe Acute Respiratory Syndrome Coronavirus (SARS-CoV), Middle East Respiratory Syndrome Coronavirus (MERS-CoV) and, most recently, SARS-CoV-2, the causative agent of COVID-19. SARS-CoV-2 emerged in China in December 2019 and subsequently spread throughout the world. Ominously, the diversity of coronavirus strains in potential animal reservoirs suggests that emerging and re-emerging pathogenic coronaviruses will continue to pose a significant threat to public health. Currently, vaccines using different platforms have been developed or are under development, and three vaccines have been authorized in the U.S. for emergency use with others expected to be available soon. A few therapeutic interventions have been given emergency use authorizations and include remdesivir (Veklury®), a combination of remdesivir and a JAK inhibitor baricitinib, and a single or a cocktail of monoclonal antibodies.

Although additional clinical trial results will be needed to fully understand the efficacy of these treatments, the currently available clinical data on these treatments showed limited effects of these treatments in reducing viral infection, disease progression, or facilitating recovery. Clinical presentation of COVID-19 patients varies from being asymptomatic to severe respiratory disease that may lead to death. Viral replication in the respiratory tract peaks during the first week of infection and decline. In severe COVID-19 cases, extensive inflammatory responses in the lungs initiated by viral replication dominate in the later stage and are the main culprit for lethality. Therefore, a combination of antiviral agents and immune modulators such as dexamethasone has been suggested to improve clinical outcome in advanced diseases. Additional potent direct-acting antiviral agents, such as protease inhibitors, are urgently required to enrich the drug arsenal against SARS-CoV-2 infection.

SUMMARY OF THE INVENTION

The COVID-19 pandemic remains a major concern for public health worldwide and there is an urgent need for the development of effective therapeutics, including vaccines, biologics, and small molecule therapeutics, to combat SARS-CoV-2, and emerging variants. The SARS-CoV-2 genome encodes two polyproteins which are processed by a 3C-like protease (3CLpro) and a papain-like protease. These viral proteases are essential for viral replication, making them attractive targets for drug development. The design of inhibitors of the protease may lead to the emergence of effective SARS-CoV-2-specific antiviral therapeutics. We previously described a series of 3CLpro inhibitors with activities against multiple coronaviruses, including SARS-CoV, MERS-CoV and more recently SARS-CoV-2 (See U.S. Pat. No. 9,474,759, and co-pending PCT/US2021/024790, filed Mar. 30, 2021, each incorporated by reference herein in their entireties). GC376 was recently demonstrated in clinical trials to have efficacy against a fatal feline coronavirus infection, feline infectious peritonitis (FIP), and is currently in clinical development for treating FLP in cats.

Here, we report 3CLpro inhibitors highly potent activity against multiple coronaviruses including FIPV and SARS-CoV-2 in enzyme and/or cell-based assays. In the mouse model of SARS-CoV-2 infection, administration of a lead compound after virus infection significantly increased survival, improved weight gain, and reduced lung virus titers and histopathology, demonstrating the proof-of-concept treatment efficacy. The results suggest the series has the potential to be developed as broad-spectrum antivirals against these important human coronaviruses as well as against other viruses that belong to the picornavirus-like supercluster, including caliciviruses and picornaviruses.

Therapeutic or prophylactic compositions are also disclosed. The compositions comprise a first a deuterated compound according to the various embodiments described herein dispersed in a pharmaceutically-acceptable carrier. A kit is also provided herein. The kit comprises: a deuterated compound according to the various embodiments described herein; and instructions for administering the compound to a subject in need thereof.

Also described herein are methods of treating or preventing viral infection. The methods can also be extended to methods of inhibiting viral infection in a subject from one or more viruses selected from the group consisting of caliciviruses, picornaviruses, and/or coronaviruses is also provided. The method comprises administering to the subject a therapeutically-effective amount of a deuterated compound according to the various embodiments described herein.

A method of preventing or inhibiting replication of a virus in a cell is also disclosed. The method comprises contacting the cell with a deuterated compound according to the various embodiments described herein, wherein the virus is selected from the group consisting of caliciviruses, picornaviruses, coronaviruses, and combinations thereof.

The invention is also concerned with the use of a deuterated compound according to the various embodiments described herein to prepare a therapeutic or prophylactic medicament for the treatment or prevention of a viral infection from caliciviruses, picornaviruses, and/or coronaviruses in a subject.

BRIEF DESCRIPTION OF THE DRAWINGS

The patent or application file contains at least one drawing executed in color. Copies of this patent or patent application

DETAILED DESCRIPTION

Figure 1:
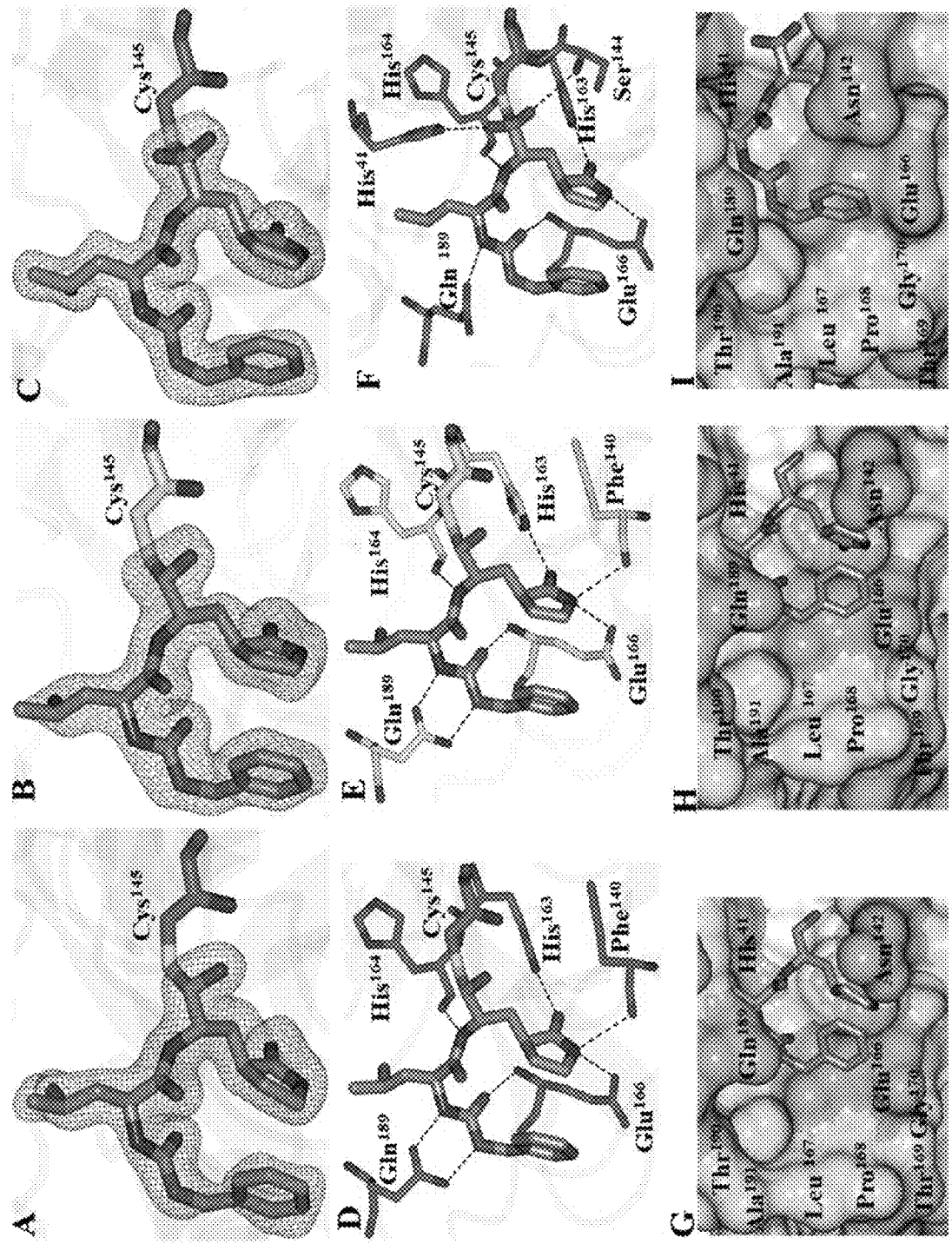
FIG. 1 shows images of cocrystal structures of SARS-CoV-2 3CLpro (A, D, G: subunit A and B, E, H: subunit B) and SARS-CoV 3CLpro (C, F, I) in complex with compound 2. Panels A-C show $F_o$-$F_c$ omit maps (green mesh) contoured at 3σ. Panels D-F show hydrogen bond interactions (dashed lines) between the inhibitor and the 3CL protease. Panels G-I show electrostatic surface representation of the binding pocket occupied by the inhibitor. Neighboring residues are colored yellow (nonpolar), cyan (polar), and white (weakly polar).

The present disclosure is concerned with antiviral compounds substituted with deuterium. Deuterium is the naturally-occurring, non-radioactive, stable isotope of hydrogen. Deuterium contains one proton, one electron, and a neutron, effectively doubling the mass as compared to hydrogen, without changing its properties significantly. Because it has reduced electronic polarizability and less hyperconjugative stabilization of adjacent bonds, it potentially can result in weaker van der Waals stabilization, and it can produce other changes in properties. Deuteration can improve the potency of compounds and also pharmacokinetic properties via various mechanisms including interfering with Cytochrome P450 enzyme-mediated clearance, lipid peroxidation and/or aldehyde oxidase-driven metabolism.

In one aspect, a deuterated antiviral compound comprising formula I, or a pharmaceutically-acceptable salt or prodrug thereof is provided:

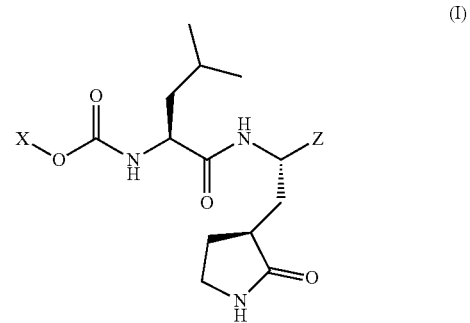

(I)

wherein, each X comprises at least one cyclic moiety, and in particular a substituted (including disubstituted) or unsubstituted $C_3$-$C_{10}$ cycloalkyl, a substituted or unsubstituted 3-7 membered heterocycle having 1-3 ring heteroatoms selected from N, O, and S, or a substituted or unsubstituted $C_{6-10}$ aryl group, each of which may be directly attached to the oxygen, or may be connected via a branched or unbranched and substituted or unsubstituted $C_1$-$C_6$ alkyl linkage, subject to the proviso that at least one of the linkage and/or the X moiety comprises a deuterium substitution; and Z is selected from the group consisting of aldehydes and bisulfite salts, or the ester or carbamate prodrugs thereof, and in particular, —CH₂OH, —CHO, —SO₃Na, —CH(OH)SO₃⁻ Na⁺, (C=O)(C=O)NHbenzyl, and —CH[O(C=O)Rw]SO₃⁻ Na⁺, where $R_w$ is an alkyl or arylalkyl with —CH₃ and —CH₂CH₃ being particularly preferred.

Using GC376 as the exemplary compound, the hydrogen groups in the metabolically active sites within the aromatic ring or in the immediately adjacent carbon group (methylene linkage) denoted via the arrows below can be substituted with deuterium to generate deuterated variants of the compounds: 1

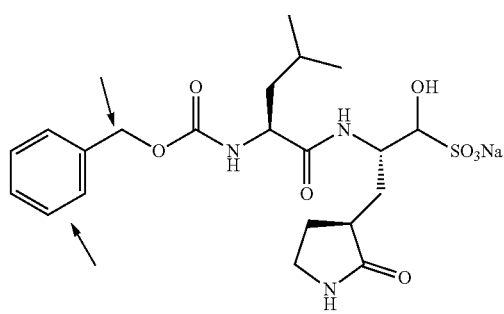

Likewise, the warhead, Z moiety, can be modified to generate prodrug forms of the compounds, which are described in detail in U.S. Pat. No. 11,033,600, filed Jan. 25, 2019, and to be issued Jun. 15, 2021, incorporated by reference herein in its entirety. The inventive approach to preparing prodrug forms of active compound can be extended to a variety of active agents. In one or more embodiments, the prodrugs are deuterated variants of ester- or carbamate-based prodrugs of inhibitors of cathepsin L, cathepsin S, calpains, or falcipain-2:

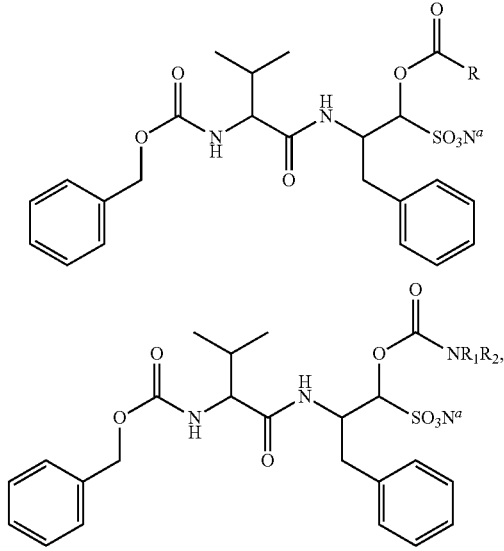

Cathepsin L prodrugs

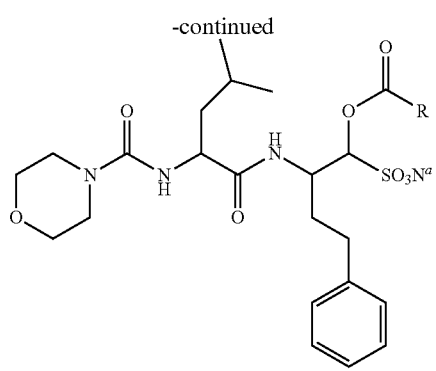

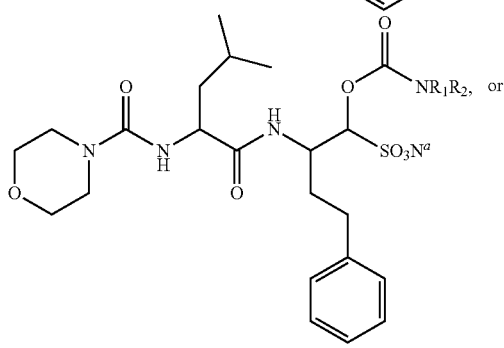

Falcipain-2 & Cathepsin L prodrugs

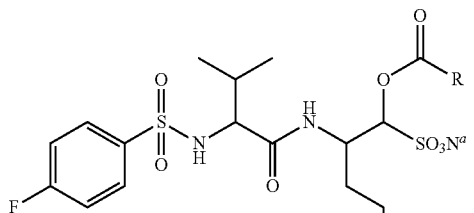

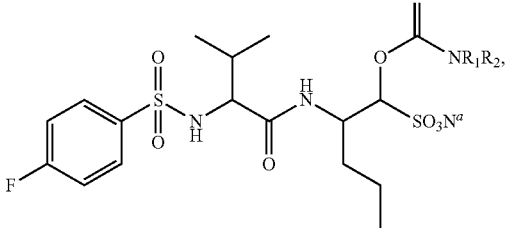

Calpain prodrugs where each R, $R_1$, and $R_2$ is defined as:
each R is selected from the group consisting of —H, branched and unbranched alkyls (preferably $C_1$-$C_8$ alkyls), substituted or unsubstituted aryls, substituted or unsubstituted arylalkyls, alkoxies, —CHR₇NHR₈, and —(CH₂)ₘW, where $R_7$ is H or a side chain of a natural or unnatural amino acid, and $R_8$ is —H, a branched or unbranched alkyl (preferably a $C_1$-$C_8$ alkyl), or carboxyalkyl, and where W is —COOR₆, —NH₂, —NHR₆, —NH(C=O)R₆, —(C=O)NH₂, or —(C=O)NHR₆, and m is 1-10 (preferably 2), and where each —R₆, is —H, a branched or unbranched alkyl (preferably a $C_1$-$C_8$ alkyl), substituted or unsubstituted phenyls, a substituted or unsubstituted aryl or a substituted or unsubstituted arylalkyl;
each $R_1$ is selected from the group consisting of —H, branched and unbranched alkyls (preferably $C_1$-$C_8$ alkyls), substituted or unsubstituted phenyls, substituted or unsubstituted aryls, substituted or unsubstituted arylalkyls, and halogenated alkyls; and each $R_2$ is selected from the group consisting of —H, branched and unbranched alkyls (preferably $C_1$-$C_8$ alkyls), substituted or unsubstituted phenyls, substituted or unsubstituted aryls, substituted or unsubstituted arylalkyls, halogenated alkyls, and —CHR$_7$COOR$_8$, where $R_7$ is H or a side chain of a natural or unnatural amino acid, and $R_8$ is H or a branched or unbranched alkyl (preferably a $C_1$-$C_8$ alkyl).

Pharmaceutically acceptable sales of any foregoing compounds can also be used. Combinations of one or more of the foregoing compounds can also be used in the invention. It should be noted that the prodrug mechanism demonstrated here can be extended to other inhibitors with warheads beyond sodium bisulfite or aldehyde, such as α-ketoamides. Examples of additional warheads are illustrated by the antiviral compounds described in U.S. Pat. No. 9,474,759, incorporated by reference herein.

In some embodiments, particularly preferred compounds comprise compounds of the formula:

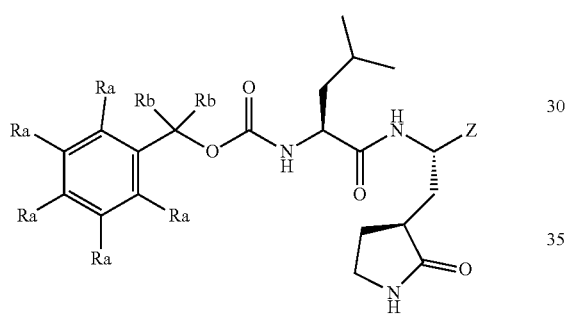

or prodrugs thereof or pharmaceutically-acceptable salts thereof, where each of $R_a$ and $R_b$, independently, is hydrogen or deuterium, provided that at least one of $R_a$ or $R_b$ is a deuterium atom and in some cases where both $R_a$ and $R_b$ are deuterium instead of hydrogen. Embodiments herein also contemplate substituted aromatic rings, where at least one $R_a$ is a halogen substitution, preferably Cl, more preferable m-Cl, and each $R_b$ is a deuterium atom. Other ring substitutions are contemplated herein for the X moiety, including nitrogen, oxygen, and sulfur substitutions.

In some embodiments, particularly preferred X moieties include the following structures in the brackets below (where the oxygen from formula (I) is depicted for clarity):

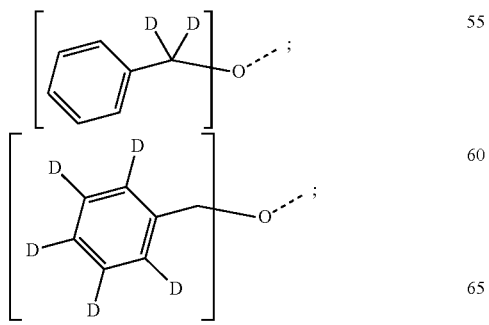

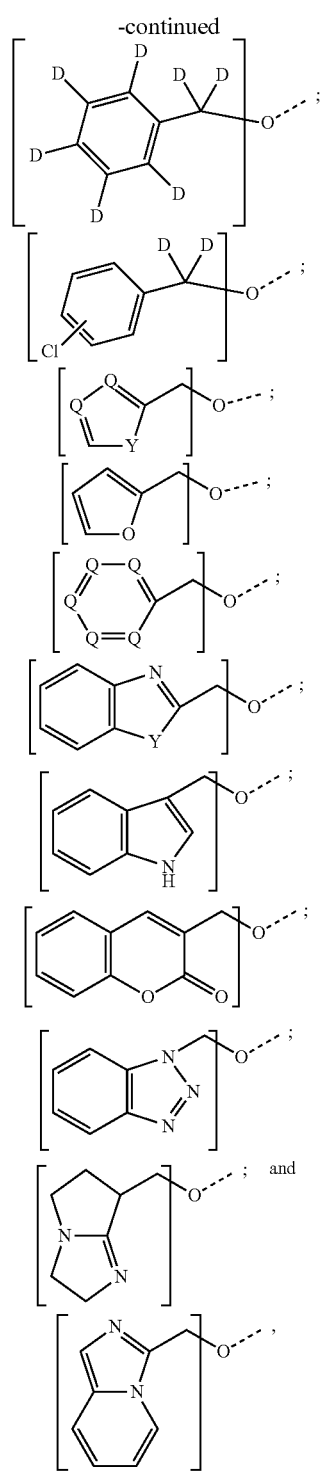

where Q is CH or N, provided that at least one Q is N subject to a maximum of three nitrogen substitutions per ring, and Y is S, NH, or O. Moreover, the methylene linkages above can be deuterated or undeuterated (except where expressly written with the deuterium substitution).

Prophylactic and/or therapeutic compositions with specific or broad-spectrum antiviral activities are also disclosed. Combinations of one or more of the foregoing compounds can also be used in the embodiments herein. The compositions comprise an antiviral compound described herein dispersed in a pharmaceutically-acceptable carrier. The term carrier is used herein to refer to diluents, excipients, vehicles, and the like, in which the antiviral may be dispersed for administration. Suitable carriers will be pharmaceutically acceptable. As used herein, the term "pharmaceutically acceptable" means not biologically or otherwise undesirable, in that it can be administered to a subject without excessive toxicity, irritation, or allergic response, and does not cause unacceptable biological effects or interact in a deleterious manner with any of the other components of the composition in which it is contained. A pharmaceutically-acceptable carrier would be selected to minimize any degradation of the compound or other agents and to minimize any adverse side effects in the subject. Pharmaceutically-acceptable ingredients include those acceptable for veterinary use as well as human pharmaceutical use, and will depend on the route of administration. For example, compositions suitable for administration via injection are typically solutions in sterile isotonic aqueous buffer. Exemplary carriers include aqueous solutions such as normal (n.) saline (~0.9% NaCl), phosphate buffered saline (PBS), sterile water/distilled autoclaved water (DAW), various oil-in-water or water-in-oil emulsions, as well as dimethyl sulfoxide (DMSO) or other acceptable vehicles, and the like.

The composition can comprise a therapeutically effective amount of the compound dispersed in the carrier. As used herein, a "therapeutically effective" amount refers to the amount that will elicit the biological or medical response of a tissue, system, or subject that is being sought by a researcher or clinician, and in particular elicit some desired therapeutic or prophylactic effect as against the viral infection by slowing and/or inhibiting 3CL protease activity and/or viral replication. One of skill in the art recognizes that an amount may be considered therapeutically "effective" even if the condition is not totally eradicated or prevented, but it or its symptoms and/or effects are improved or alleviated partially in the subject. In some embodiments, the composition will comprise from about 5% to about 95% by weight of an antiviral compound described herein, and preferably from about 30% to about 90% by weight of the antiviral compound, based upon the total weight of the composition taken as 100% by weight. In some embodiments, combinations of more than one type of the described antiviral compounds can be included in the composition, in which case the total levels of all such compounds will preferably fall within the ranges described above.

Other ingredients may be included in the composition, such as adjuvants, other active agents, preservatives, buffering agents, salts, other pharmaceutically-acceptable ingredients. The term "adjuvant" is used herein to refer to substances that have immunopotentiating effects and are added to or co-formulated in a therapeutic composition in order to enhance, elicit, and/or modulate the innate, humoral, and/or cell-mediated immune response against the active ingredients. Other active agents that could be included in the composition include other antiviral compounds (e.g., cathepsins) or any immunogenic active components (e.g., antigens) such as those that resemble a disease-causing microorganism or infectious agent, and/or are made from weakened or killed forms of the same, its toxins, subunits, particles, and/or one of its surface proteins, such that it provokes an immune response to that microorganism or infectious agent. In addition to live, modified, or attenuated vaccine components, active agents using synthetic peptides, carbohydrates, or antigens can also be used.

Compositions according to the embodiments disclosed herein are useful in inhibiting protease activity. More specifically, the compositions can be used to inhibit viral infection or viral replication, such as by treating and/or preventing viral infection from a variety of causes, including caliciviruses (noroviruses), picomaviruses, and/or coronaviruses in a subject. Viruses in the picomavirus-like supercluster include important human and animal pathogens. For example, caliciviruses include noroviruses (Norwalk virus [NV]), feline calicivirus, MD145, murine norovirus [MNV], vesicular exanthema of swine virus, and rabbit hemorrhagic disease virus. Picomaviruses include enteroviruses (such as enterovirus 71), poliovirus, coxsackievirus, foot-and-mouth disease virus (FMDV), hepatitis A virus (HAV), porcine teschovirus, and rhinovirus (cause of common cold). Coronaviruses include human coronavirus (cause of common cold such as 229E strain), transmissible gastroenteritis virus (TGEV), murine hepatitis virus (MHV), bovine coronavirus (BCV), feline infectious peritonitis virus (FIPV), severe acute respiratory syndrome coronavirus (SARS-Co), SARS-CoV2 (causative agent of COVID-19), and Middle East respiratory syndrome coronavirus (MERS-CoV).

Other conditions that can be targets for treatment through inhibition of protease activity include conditions ameliorated by targeting cathepsins, falcipains, and/or calpains, such as malaria, tumor cells, stroke, heart attack, neural degeneration, cataracts, and glaucoma.

Thus, embodiments described herein have broad-spectrum therapeutic and/or prophylactic uses. The terms "therapeutic" or "treat," as used herein, refer to processes that are intended to produce a beneficial change in an existing condition (e.g., viral infection, disease, disorder) of a subject, such as by reducing the severity of the clinical symptoms and/or effects of the infection, and/or reducing the duration of the infection/symptoms/effects. The terms "prophylactic" or "prevent," as used herein, refer to processes that are intended to inhibit or ameliorate the effects of a future viral infection or disease to which a subject may be exposed (but is not currently infected with). In some cases, the composition may prevent the development of observable morbidity from viral infection (i.e., near 100% prevention). In other cases, the composition may only partially prevent and/or lessen the extent of morbidity due to the viral infection (i.e., reduce the severity of the symptoms and/or effects of the infection, and/or reduce the duration of the infection/symptoms/effects, or increase the rate of recovery from the condition). In either case, the compounds are still considered to "prevent" the target infection or disease.

In use, a therapeutically-effective amount of a deuterated antiviral compound is administered to a subject. In some embodiments, a composition comprising a therapeutically-effective amount of a deuterated antiviral compound is administered to a subject. Regardless, the compound or pharmaceutically acceptable salt or prodrug thereof will preferably be administered to the subject in an amount sufficient to provide antiviral compound levels (independent of salt, if any) of from about 0.1 mg to about 1,000 mg of compound per kg of body weight of the subject, preferably from about 1 mg/kg to about 100 mg/kg of body weight of the subject, and more preferably from about 10 mg/kg to about 50 mg/kg of body weight of the subject. Thus, it will be appreciated that in the case of compound salts, for example, the formulation may be administered in amounts greater than the above ranges to provide sufficient levels of the active compound.

In some embodiments, upon administration, the prodrug mechanism of action entails enzyme-mediated, chemical, or spontaneous degradation or hydrolysis that converts the prodrug into an active metabolite (in some cases involving one or more intermediate compounds). For example, in the case of the bisulfite adducts described herein, the prodrugs I or II are converted into the aldehyde bisulfite adduct which subsequently reverts to the precursor aldehyde (active metabolite). In some cases, intermediate compounds may also have inhibitory activity towards the target, such as by functioning as a transition state mimic. In the case of aldehydes, subsequent reaction with the catalytic cysteine (Cys139) of norovirus 3CLpro leads to inactivation of the enzyme via the formation of a tetrahedral adduct. The rate and extent of absorption can be modulated by varying the hydrophobic components and the use of natural and unnatural amino acid side chains. Encapsulation techniques can also be used to facilitate delivery of the prodrug.

In some embodiments, the deuterated compound or compositions can be provided in unit dosage form in a suitable container. The term "unit dosage form" refers to a physically discrete unit suitable as a unitary dosage for human or animal use. Each unit dosage form may contain a predetermined amount of the deuterated compound (and/or other active agents) in the carrier calculated to produce a desired effect. In other embodiments, the deuterated compound can be provided separate from the carrier (e.g., in its own vial, ampule, sachet, or other suitable container) for on-site mixing before administration to a subject. A kit comprising the deuterated antiviral compound(s) is also disclosed herein. The kit further comprises instructions for administering the deuterated compound to a subject. The deuterated antiviral compound(s) can be provided as part of a dosage unit, already dispersed in a pharmaceutically-acceptable carrier, or it can be provided separately from the carrier. The kit can further comprise instructions for preparing the deuterated antiviral compounds for administration to a subject, including for example, instructions for dispersing the deuterated compounds in a suitable carrier.

In some embodiments, the subject is afflicted with or suffering from a condition (e g , infection, disease, or disorder) before the deuterated compounds are administered, wherein methods described herein are useful for treating the condition and/or ameliorating the effects of the condition. Preferably, the antiviral compound is administered as soon as possible after infection, preferably within about 7 days from onset of observable symptoms, more preferably within about 5 days from onset of observable symptoms, even more preferably within 3 days from onset of observable symptoms or known contact with virus. It will be appreciated that the sooner the deuterated compound(s) is administered, the increased chance of successfully reducing effects of the viral infection. In other embodiments, the subject is free of a given condition before administering the deuterated compound, wherein the methods described herein are useful for preventing the occurrence or incidence of the condition and/or preventing the effects of the condition, as described above. Thus, the deuterated compounds can be given prophylactically (before observable infection) or therapeutically (after observable infection).

The disclosed embodiments are suitable for various routes of administration, depending upon the particular carrier and other ingredients used. For example, the prophylactic and/or therapeutic deuterated compounds or compositions can be injected intramuscularly, subcutaneously, intradermally, or intravenously. They can also be administered via mucosa such as intranasally or orally. The deuterated compounds or compositions can also be administered through the skin via a transdermal patch.

It will be appreciated that therapeutic and prophylactic methods described herein are applicable to humans as well as any suitable animal, including, without limitation, dogs, cats, and other pets, as well as, rodents, primates, horses, cattle, pigs, etc. The methods can be also applied for clinical research and/or study. Additional advantages of the various embodiments of the disclosure will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described and claimed herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone, B alone, C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration, and nothing therein should be taken as a limitation upon the overall scope of the invention.

Example 1

In preliminary work, we have generated and screened various versions of protease inhibitors (including GC373 and GC376) containing deuterium substitutions, and showed they have comparable or better potency than parental compounds (GC373 and GC376) against coronaviruses (FIPV and SARS-CoV2). The deuterated prodrug forms were also generated and examined for the potency against coronaviruses (see Table 1).

TABLE 1

Inhibitory activity of deuterated compounds.

| Compound | FIPV (EC$_{50}$ uM) (cell culture) | SARS-CoV2 (EC$_{50}$ uM) (enzyme) | Note |
|---|---|---|---|
| GC373 | 0.05 | 0.5 | Parental aldehyde |
| GC376 | 0.05 | 0.5 | BS of GC373 |
| GC1126 | 0.05 | 0.1 | Deuterated GC373-No1 |
| GC1128 | 0.05 | 0.15 | Deuterated GC373-No2 |

TABLE 1-continued

Inhibitory activity of deuterated compounds.

| Compound | FIPV (EC$_{50}$ uM) (cell culture) | SARS-CoV2 (EC$_{50}$ uM) (enzyme) | Note |
|---|---|---|---|
| GC1127 | 0.08 | 0.12 | Deuterated GC376-No1 |
| GC1129 | 0.06 | 0.16 | Deuterated GC376-No1 |
| GC1130 | 0.06 | 0.7 | Prodrug of GC1129-No1 |
| GC1131 | 0.06 | 0.8 | Prodrug of GC1129-No2 |

It will be appreciated that this approach may be applied to adjust the efficacy and pharmacokinetics of the various protease inhibitor compounds and their prodrugs, which have been synthesized as part of this ongoing work.

Example 2

Introduction

Protease inhibitors targeting viral 3C-like protease are attractive therapeutic options for COVID-19. Here, we synthesized deuterated variants of a coronavirus protease inhibitor GC376 and determined the therapeutic efficacy in a lethal mouse model. The transgenic mice infected with SARS-CoV-2, a causative agent of COVID-19, develop lung pathology resembling that of severe COVID-19 patients and were used for antiviral drug testing. The deuterated variants of GC376 have improved potency against SARS-CoV-2 in in vitro assays. Furthermore, treatment with a deuterated variant starting at 24 hr post-infection resulted in significantly increased survival of mice, compared to vehicle-treated mice. The results suggest that deuterated variants have excellent potential as antiviral agents against SARS-CoV-2.

Some mice that express human ACE2 or hamsters develop weight loss and lung histopathology, but they have no or little mortality following human SARS-CoV-2 infection. Thus, they serve as good models for asymptomatic, mild, and moderate SARS-CoV-2 infection and for studies of viral transmission. Currently only a few fatal infection animal models are available that can recapitulate the key features of severe pathogenesis in humans with COVID-19. Transgenic hACE2-HFH4 mice and K18-hACE2 mice, which express human angiotensin I-converting enzyme 2 (ACE2) receptor under HFH4 or K18 promoter or a mouse-adapted SARS-CoV-2 MA10 strain can lead to fatality dependent upon virus challenge doses. Neural invasion of the brain variably occurs in hACE2 transgenic mice and is associated with a fatal outcome. In the absence of brain infection, however, the respiratory infection is still lethal, depending on initial virus inoculum. Although, there is evidence of neurological complications, such as encephalopathy and encephalitis, in COVID-19 patients, the relevance of brain infection in these animal models in human neurological disease needs further clarification. The fatal infection models are useful models for efficacy testing of antiviral agents as they show viral replication in the lungs with inflammation and virus-induced histopathological changes that resemble severe COVID-19 infection in humans. In the K18-hACE2 model, pre- and post-infection treatment efficacy of human convalescent plasma (CP) from a recovered COVID-19 patient was previously studied, and antiviral agents such as GC376 were tested. We report herein the results of our studies related to the synthesis and evaluation of deuterated GC376 variants which have enhanced antiviral activity and display efficacy in a fatal mouse model (K18-hACE2 mice) of SARS-CoV-2.

Results

Deuterated variants of GC376 display potent inhibitory activity against SARS-CoV-2 in the enzyme and the cell-based assays. We synthesized deuterated variants based on GC376 and compared their inhibitory activities against SARS-CoV-2 to non-deuterated GC376 in the enzyme and the cell-based assays (Table 2).

TABLE 2

Structures and inhibitory activities of deuterated variants of GC376 against SARS-CoV-2 in the enzyme and cell-based assays.

| | | | SARS-CoV-2 Testing | | |
|---|---|---|---|---|---|
| | | | | EC$_{50}$ (µM) | |
| | Compound | Z | IC$_{50}$ (µM) | VeroE6 | A549-ACE2 | CC$_{50}$ (µM) |
| Group A - Alcohol inputs (X moiety) <br> (benzyl-CD$_2$OH) | | | | | | |
| 1 | CHO | | 0.17 ± 0.05 | 0.068 ± 0.01 | 0.086 ± 0.01 | >100 |
| 2 | CH(OH)SO$_3$Na | | 0.18 ± 0.04 | 0.086 ± 0.02 | 0.069 ± 0.01 | >100 |
| 3 | CH(O(C=O)CH$_3$)SO$_3$Na | | 0.71 ± 0.06 | N/D* | N/D | >100 |
| 4 | CH(O(C=O)n-pentyl)SO$_3$Na | | 0.80 ± 0.1 | N/D | ND | >100 |
| 5 | (C=O)(C=O)NHbenzyl | | 1.31 ± 0.55 | N/D | MD | >100 |

TABLE 2-continued

Structures and inhibitory activities of deuterated variants of GC376 against SARS-CoV-2 in the enzyme and cell-based assays.

[Structure: X-O-C(=O)-NH-CH(CH2CH(CH3)2)-C(=O)-NH-CH(Z)-CH2-(2-oxopyrrolidin-3-yl)]

SARS-CoV-2 Testing

| Compound | Z | $IC_{50}$ (μM) | $EC_{50}$ (μM) VeroE6 | $EC_{50}$ (μM) A549-ACE2 | $CC_{50}$ (μM) |
|---|---|---|---|---|---|
| Group B - Alcohol inputs (X moiety) | | | | | |
| [Structure: benzyl alcohol with 4 D's on ring, CD2OH] | | | | | |
| 6 | CHO | 0.16 ± 0.03 | 0.077 ± 0.01 | 0.075 ± 0.01 | >100 |
| 7 | CH(OH)SO$_3$Na | 0.19 ± 0.04 | 0.079 ± 0.01 | 0.10 ± 0.01 | >100 |
| 8 | CH(O(C=O)n-pentyl)SO$_3$Na | 0.68 ± 0.35 | N/D | N/D | >100 |
| Group C - Alcohol inputs (X moiety) | | | | | |
| [Structure: benzyl alcohol with 4 D's on ring, CD2OH] | | | | | |
| 9 | CHO | 0.24 ± 0.01 | N/D | N/D | >100 |
| 10 | CH(OH)SO$_3$Na | 0.21 ± 0.02 | N/D | N/D | >100 |
| 11 | CH(O(C=O)n-pentyl)SO$_3$Na | 0.77 ± 0.12 | N/D | N/D | >100 |
| GC376* | | 0.41 ± 0.07 | 0.23 ± 0.01 | N/D | >100 |

*Currently in clinical development, see U.S. Patent No. 9,474,759, issued October 25, 2016, incorporated by reference herein in its entirety. The activity and cytotoxicity of deuterated variants of G-C376 was tested.

$IC_{50}$, the 50% inhibitory concentration determined in the enzyme assay;

$EC_{50}$, the 50% effective concentration determined in Vero E6 cells; and $CC_{50}$, the 50% cytotoxic concentration determined in Vero E6 and CRFK cells.

The values indicate the means and the standard deviations of the means.

Three different variants of deuterated aldehyde compounds (compounds 1, 6 and 9 with $R_1$, $R_2$ and $R_3$, respectively) as well as their bisulfite adducts (compounds 2, 7 and 10) were prepared for the testing. In addition, an α-ketoamide (compound 5) based on compound 1 and prodrug variations (compounds 3, 4, 8 and 11) of the bisulfite adducts of aldehydes (compounds 1, 6 and 9) were synthesized for the testing. In the enzyme assay, the bisulfite adducts showed similar 50% inhibitory concentration ($IC_{50}$) values as their aldehyde counterparts (Table 2). The α-ketoamide derivative (compound 5) of compound 1 had markedly decreased potency in the enzyme assay. Likewise, prodrug counterparts (compounds 3, 4, 8 and 11) have significantly increased $IC_{50}$ values compared to their aldehyde and bisulfite precursors (Table 2). The deuterated compounds that were more effective than GC376 in the enzyme assay were tested in the cell-based assay using VeroE6 and A549-ACE2 cell lines. The 50% effective concentration ($EC_{50}$) values of the tested deuterated compounds (compounds 1, 2, 6 and 7) (0.068 to 0.086 μM) were comparable in those cell lines and lower than GC376 by 2.67-3.38-fold in Vero E6 cells. All compounds, including GC376, did not show any cytotoxicity up to 100 μM (Table 2).

Figure 5:
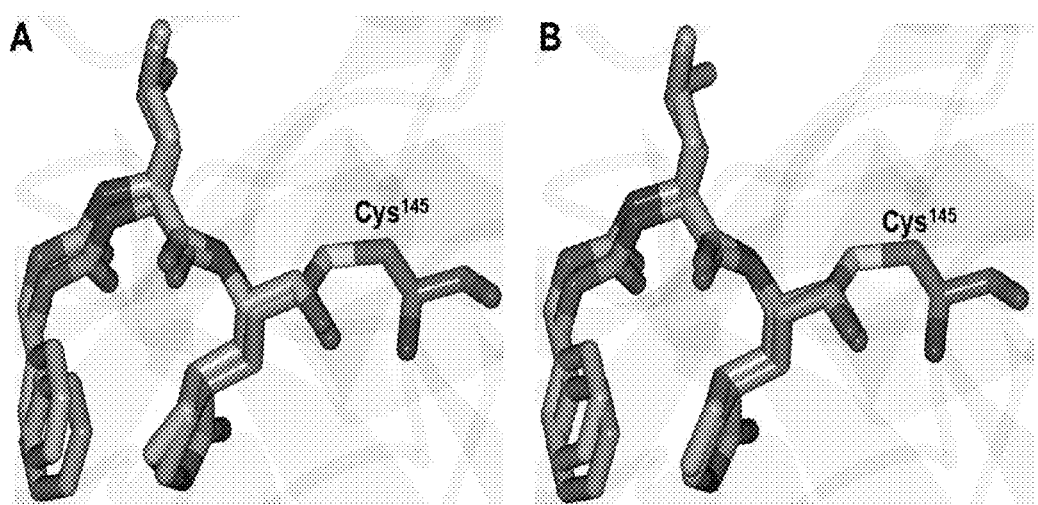
FIG. 5 shows structures of SARS-CoV-2 3CLpro in complex with compound 2 (gray) superimposed with (A) SARS-CoV-2 3CLpro with GC376 (PDB 6WTJ, gold) and (B) SARS-CoV-2 3CLpro with GC373 (PDB 6WTK, coral).

Structures of 3CLpro of SARS-CoV and SARS-CoV-2 bound with deuterated variants of GC376. Compound 2 with a bisulfite adduct warhead and compound 5 with α-ketoamide were co-crystallized with the 3CLpro of SARS-CoV-2 and SARS-CoV and examined by X-ray crystallography. Examination of the active site of SARS-CoV-2 3CLpro revealed the presence of prominent difference electron density consistent with compound 2 covalently bound to the Sγ atom of $Cys^{145}$ in each subunit (FIGS. 1A and B). Interestingly, the electron density was most consistent with the S-enantiomer at the newly formed stereocenter. Although the electron density in subunit B did contain a small "bulge" that may be due to the R-enantiomer, only one configuration was modeled. Compound 2 adopts the same binding mode in each subunit and forms identical hydrogen bond interactions with residues $Phe^{140}$, $His^{163}$, $His^{164}$, $Glu^{166}$ and $Gln^{189}$ (FIGS. 1D and E). As we generally observed in studies of SARS-CoV 3CLpro, the electron density map was consistent with both the R and S-enantiomers of compound 2 at the new stereocenter formed by covalent attachment of the Sγ atom of $Cys^{145}$ in the cocrystal structure of SARS-CoV 3CLpro (FIG. 1C). Overall, the hydrogen bond interactions are nearly identical relative to SARS-CoV-2 3CLpro. The main difference is that a hydrogen bond is formed between $His^{41}$ and the hydroxyl of compound 2 in the R-enantiomer and a long contact (3.29 Å) to the backbone N-atom of $Ser^{144}$ with the hydroxyl of the S-enantiomer (FIG. 1F). Notably, the hydroxyl in compound 2 bound to SARS-CoV-2 3CLpro is 3.38 Å and 3.39 Å from the N-atom of $Ser^{144}$, which would be a weak hydrogen bond contact. The benzyl ring in both structures is positioned outward from the hydrophobic $S_4$ subsite and are directed towards the surface as shown in FIGS. 1G, H and I. Notably, the structures of SARS-CoV-2 3CLpro in complex with non-deuterated G376 and its precursor aldehyde GC373 (PDB 6WTJ and 6WTK, respectively) adopts the same binding mode as that observed for compound 2 (FIG. 5). Superposition yielded root-mean-square deviation (RMSD) deviations of 0.59 Å (GC376) and 0.55 Å (GC373) between Cα atoms for 299 residues aligned.

Figure 6:
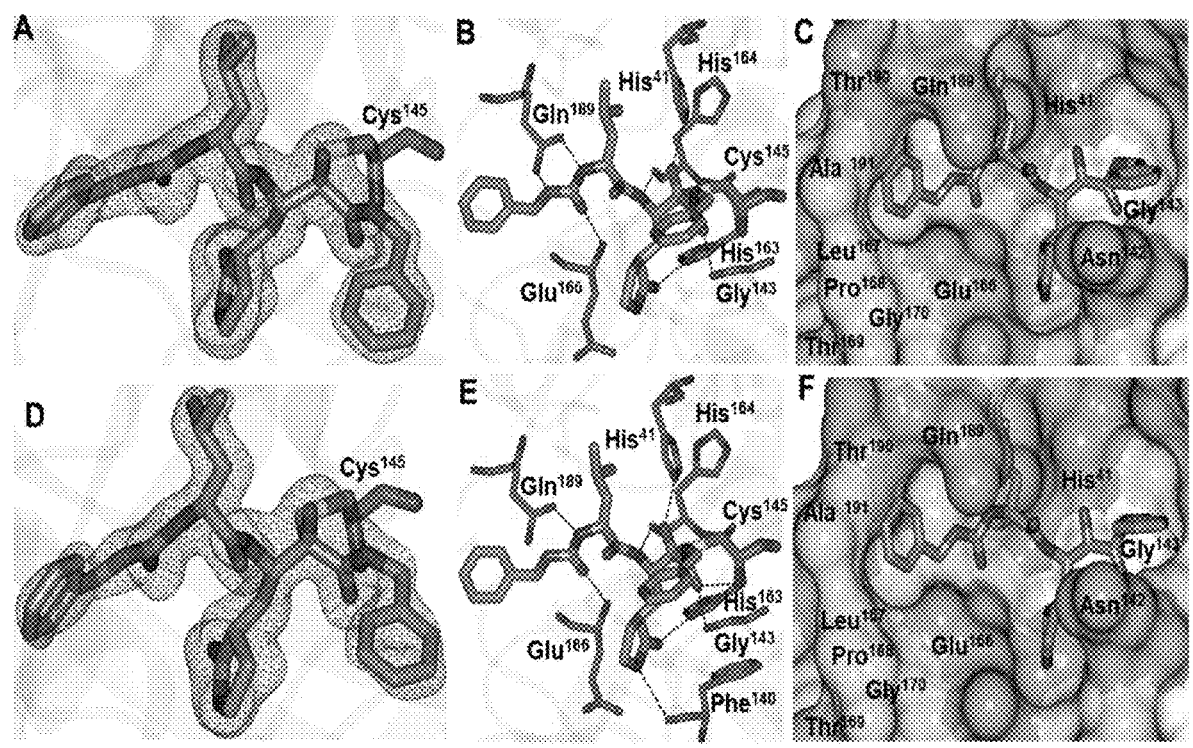
FIG. 6 shows cocrystal structures of SARS-CoV 3CLpro (A, B, C) and SARS-CoV-2 3CLpro (D, E, F) in complex with compound 5. Panels A and D show $F_o$-$F_c$ omit maps (green mesh) contoured at 3σ. Panels B and E show hydrogen bond interactions (dashed lines) between the inhibitor and the 3CL protease. Panels C and F show electrostatic surface representation of the binding pocket occupied by the inhibitor. Neighboring residues are colored yellow (nonpolar), cyan (polar), and white (weakly polar).
Figure 7:
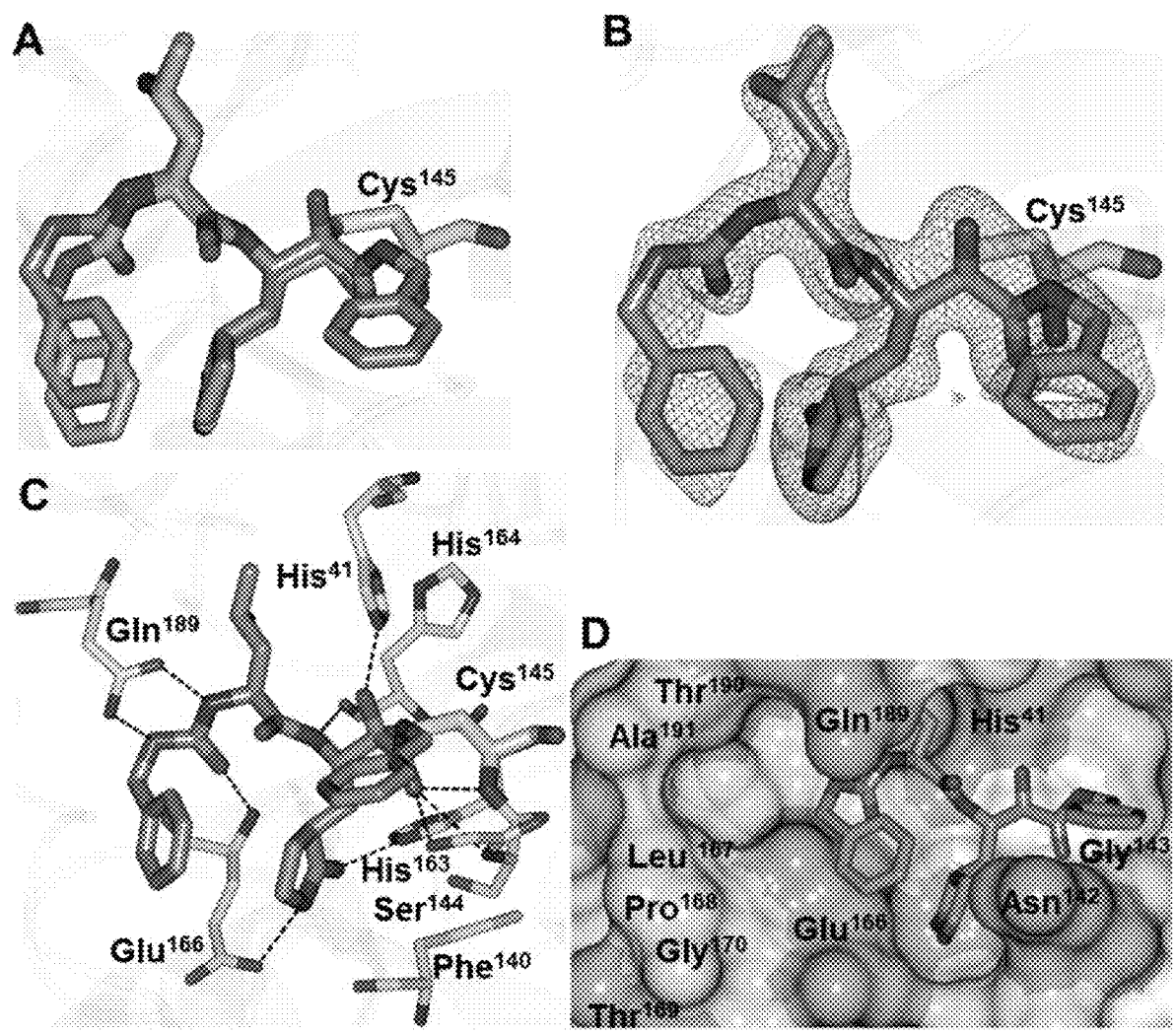
FIG. 7 shows the structure of SARS-CoV-2 3CLpro in complex with compound 5 associated with subunit B. (A) Structure of compound 2 (gold) superimposed onto compound 5 in subunit B (gray) showing the similar binding modes. (B) $F_o$-$F_c$ omit map (green mesh) contoured at 3σ. (C) Hydrogen bond interactions (dashed lines) between the inhibitor and the 3CL protease. (D) Electrostatic surface representation of the binding pocket occupied by the inhibitor. Neighboring residues are colored yellow (nonpolar), cyan (polar), and white (weakly polar).

The structures of SARS-CoV and SARS-CoV-2 3CLpro in complex with compound 5 also contained prominent difference in electron density consistent with the inhibitor covalently bound to the Sγ atom of $Cys^{145}$ (FIGS. 6A and D). The entire inhibitor could be modeled in subunit A but was partially disordered in subunit B and the benzyl group in the $S_4$ subsite could not be modeled for SARS-CoV. The inhibitor forms direct hydrogen bond interactions similar to compound 2 as shown in FIGS. 6B and E. The benzyl group in subunit A of both SARS-CoV and SARS-CoV-2 3CLpro is positioned near hydrophobic residues within the $S_4$ subsite (FIGS. 6C and F). The benzyl ring in the α-ketoamide region of the inhibitor is positioned near a cleft formed by $Asn^{142}$/$Gly^{143}$ in both structures. Interestingly, the compound bound to subunit B of SARS-CoV-2 3CLpro adopts a conformation similar to that observed for compound 2 in which the benzyl group is directed away from the $S_4$ subsite and towards the surface (FIG. 7). Therefore, it appears the structure of SARS-CoV-2 3CLpro in complex with compound 5 serendipitously contains two binding modes of the inhibitor.

Figure 2:
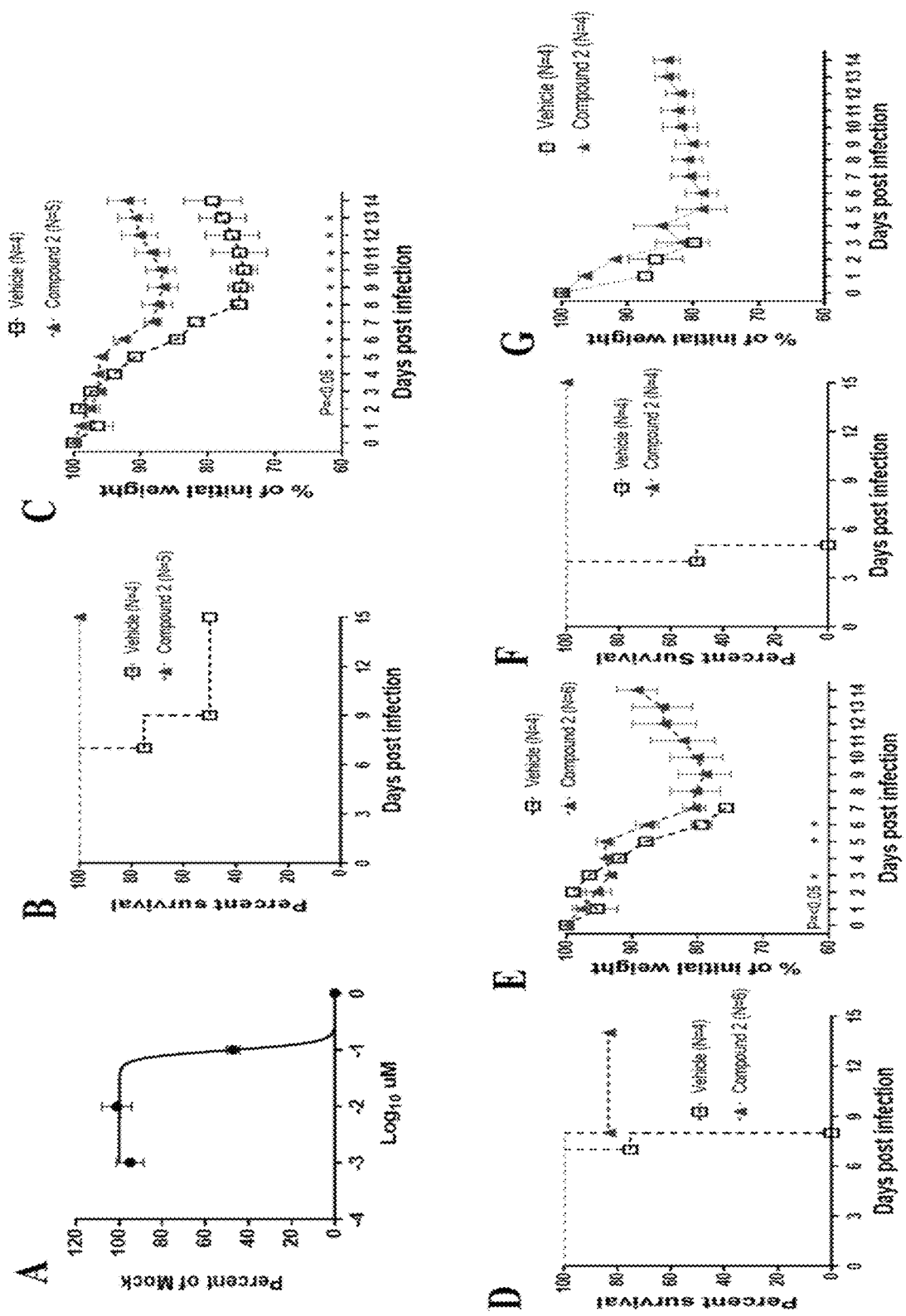
FIG. 2 shows the data from therapeutic treatment of K18-hACE2 mice infected with SARS-CoV-2. (A) A dose-dependent curve for compound 2 against SARS-CoV-2 in cell culture. Confluent Vero E6 cells were inoculated with SARS-CoV-2, and medium containing various concentrations of compound 2 and agar was applied to the cells. After 48-72 hr, plaques in each well were counted, and $EC_{50}$ values were determined by GraphPad Prism software. (B and C) The K18-hACE2 mice infected with SARS-CoV-2 with 2×10³ plaque forming unit (pfu)/mouse were treated with compounds 2 at 100 mg/kg once per day or vehicle starting at 1-day post-infection (dpi) for up to 10 days, and survival (B) and weight (C) were monitored for 15 days. (D to F) In two separate experiments, the K18-hACE2 mice infected with SARS-CoV-2 with 5×10 pfu/mouse were treated with compound 2 at 125 mg/kg once per day or vehicle starting at 1 dpi for up to 10 days, and survival (D and G) and weight (E and F) were monitored for 15 days. The data points represent the means and the standard deviations of the means. The analysis of survival curves between groups was performed using a Log-rank (Mantel-Cox) test in GraphPad Prism software. The symbols and the bars in Panels C and E represent the means and the standard deviations of the means. Asterisks indicate statistical difference between vehicle and compound 2-treated groups determined using multiple T-test in GraphPad Prism software ($p<0.05$).

Treatment with compound 2 at 24 hrs after SARS-CoV-2 infection demonstrates efficacy against fatal SARS-CoV-2 infection in K18-HACE2 mice. Compound 2 was tested in SARS-CoV-2-infected K18-hACE2 mice for protective efficacy, because it potently inhibited SARS-CoV-2 in the cell-based assay described above. The dose curve of compound 2 against SARS-CoV-2 in cell culture is shown in FIG. 2A. In the first experiment, infection with $2\times10^3$ pfu per mouse led to body weight loss in all vehicle-treated mice resulting in 50% survival by 9 dpi (FIG. 2B). Mice treated with compound 2 (100 mg/kg/day, once a day) starting from 24 hr post infection (1 dpi) lost body weight, but loss was less severe compared to vehicle-treated mice with statistically significant differences ($0.002<p<0.049$) on most days between 5-10 dpi (FIG. 2C). All compound 2-treated mice gradually gained body weight and were alive at the end of the study (15 dpi) (FIG. 2C), although survival of these mice was not statistically different (p 0.18) compared to vehicle-treated mice, likely due to lower fatality of control mice. In the second and third experiment, a higher virus challenge dose ($5\times10^3$ pfu per mouse) was given before treatment with vehicle or compound 2 (125 mg/kg/day, once a day) started 24 hr post infection. In the second experiment, the vehicle-treated mice exhibited greater body weight loss than those with the lower virus challenge (experiment 1), and none of the mice (N=4) survived past 7 dpi (FIG. 2D). Weight losses of mice treated with compound 2 were significantly less than those with vehicle treatment at 3, 5, and 6 dpi ($0.009<p<0.017$), and compound 2-treated mice started to gain weight from 10 dpi (FIG. 2E). In contrast to 0% survival in vehicle-treated mice, 5 out of 6 compound 2-treated mice (83%) survived at the end of the study (15 dpi), resulting in significant improved survival of compound 2-treated mice (P=0.011). In the third experiment, although the vehicle- or compound 2-treated mice did not show a statistically difference in body weight loss for 0-5 dpi, compound 2-treated mice started gaining weight from 6-7 dpi (FIG. 2F). All compound 2-treated mice survived at the end of the study (15 dpi), while all vehicle-treated mice died by 5 dpi (P=0.0084).

Figure 3:
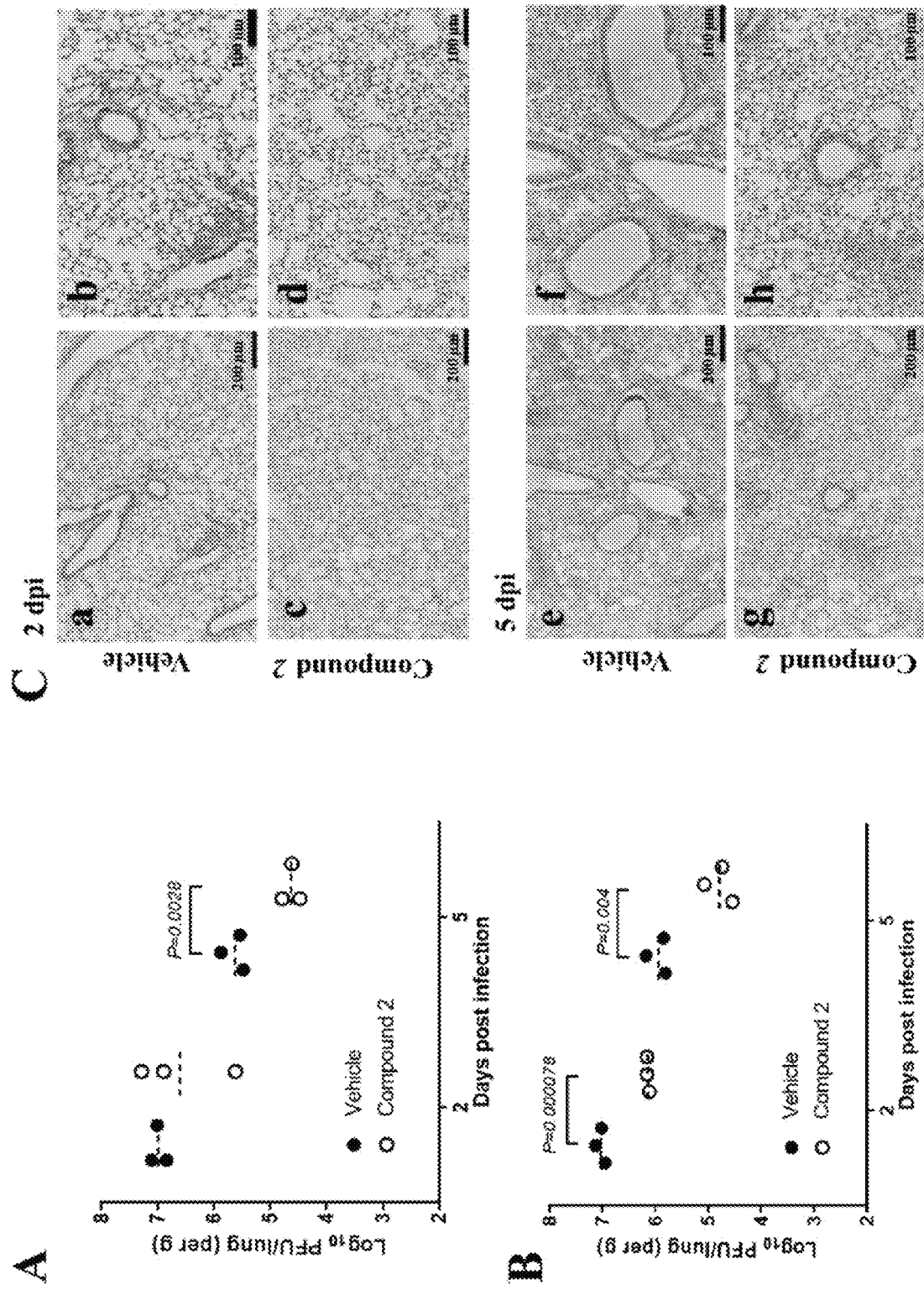
FIG. 3 shows the data from lung virus titers and histopathology of K18-hACE2 mice infected with SARS-CoV-2 and treated with vehicle or compound 2 starting at 1-day post infection (dpi). The lungs and the brains were collected at 2 and 5 dpi for virus titration (A and B) and histopathology (C). (A and B) Lung virus load in vehicle- or compound 2-treated groups in two separate experiments. Each symbol represents individual mouse, and the dashed line represents the means while the dotted line is the limit of detection (200 plaque forming unit, pfu). Confluent Vero E6 cells were inoculated with serial dilutions of lung homogenates and agar was applied to the cells. After 48-72 hr, plaques in each well were counted and pfu per gram was calculated. Statistical significance was determined using multiple T-test in GraphPad Prism software ($p<0.05$). (C) Lungs were examined for edema and for hyaline membrane formation. Lung sections were stained with hematoxylin and eosin for histopathology at 2 (a to d) or 5 dpi (e to h). Histopathology images are shown at either 10× (a, c, e, and g) with a 200 μm scale bar or 20× (b, d, f, and h) with a 100 μm scale bar for vehicle control (a, b, e, and f) and compound 2-treat groups (c, d, g, and h).

Treating infected K18 HACE2 mice with compound 2 reduces viral titers and histopathological changes in the lungs. In two separate experiments, mice were infected with $5\times10^3$ pfu SARS-CoV-2 virus and treated with compound 2 or vehicle starting from 1 dpi (24 hr post infection). In both experiments, lung virus titers peaked at 2 dpi and decreased at 5 dpi in both groups. Virus titers were statistically lower in compound 2-treated mice compared to vehicle-treated mice at 5 dpi by approximately 10.54 to 13.57-fold in both experiments (P=0.0028 and 0.004, respectively) (FIGS. 3A and B), although statistically significant reduction of virus titers was also observed at 2 dpi in the second experiment (P=0.004) (FIG. 3B). Lung pathology in vehicle-treated mice obtained from the first experiment included diffuse alveolar damage with progressive alveolar or interstitial lesions characterized by edema, inflammation and focal cytomegaly in some alveolar lining cells. Additional features include an accumulation of immune effector cells, including granulocytes and macrophages, evidence of cell death, hemorrhage, hyaline membranes, and occasional vascular thrombi. Histopathological observations were in agreement with improved survival observed in SARS-CoV-2 infected animals treated with compound 2 (FIG. 3C). At 2 dpi, alveolar edema was seen in some lung tissue sections (average score 0.5) in the lungs from animals treated with vehicle (FIG. 3C a and b), but there were few lesions in the lungs from compound 2-treated animals (average score 0) (FIG. 3C c and d). Mild perivascular infiltrates were seen in lungs from both vehicle and compound 2-treated animals at 2 dpi (FIG. 3C a-d). At 5 dpi, while severe edema (average score 4) and perivascular infiltrates (average score 3.5) were evident in the lungs from vehicle-treated animals (FIG. 3C e and f), mild edema (average score 2) and perivascular infiltrations (average score 2) were observed in the lungs of compound 2-treated animals (FIG. 3C g and h). K18-hACE2 mice infected with SARS-CoV-2 sometimes develop encephalitis. Low levels of virus (340, 1660 and 660 PFU/brain) but no pathological changes were detected in vehicle-treated mice. In contrast, neither pathological changes nor infectious virus was detected at 2 and 5 dpi in the brains of mice treated with compound 2 (detection limit: 200 PFU/g)

DISCUSSION

The advent of SARS-CoV-2, the causative agent of COVID-19, has provided the impetus behind worldwide efforts to develop effective countermeasures against the virus for the treatment of COVID-19, including the use of repurposed drugs. Indeed, remdesivir, a nucleoside analogue, which was originally developed and FDA-approved for treating Ebola virus infection has been shown to be a potent inhibitor of SARS-CoV-2 and recently approved for COVID-19. However, effects in patients have been modest, with some studies showing no efficacy. Multiple FDA-approved drugs which exert their antiviral effects by impeding key steps in the viral lifecycle, including virus entry and fusion, and viral replication, among others, are currently under intense investigation for use against SARS-CoV-2. Efforts in developing small molecule inhibitors targeting the virus proteases of SARS-CoV-2 have focused on blocking 3CLpro. Recently, GC376, a 3CL protease inhibitor under commercial development for FIP, was reported to have anti-S ARS-CoV-2 activity in several studies, which suggests this compound is a lead compound for COVID-19 amenable to further optimization.

The in vitro antiviral effects of GC376 are comparable to other remdesivir and other nucleoside analogues and protease inhibitors under development against SARS-CoV-2. The antiviral compounds, including GC376, showed antiviral effects against SARS-CoV-2 in human ACE-2 expressing transgenic mice or in rhesus macaque with non-lethal infection. However, few reports are available on the effects of these compounds in animal models with lethal infection. In a report where GC376 was given three hours after virus inoculation that led to 100% fatality, there was no difference in survival of K18 mice, although reduced viral load and inflammation was observed in the lungs compared to vehicle-treated controls.

It was envisaged here that deuterated variants of GC376 could function as therapeutics with superior characteristics compared to the corresponding non-deuterated GC376 drug. Deuterated small compounds contain one or more deuterium, a heavier nonradioactive isotope of hydrogen, as a chemical element in place of hydrogen. Higher mass of deuterium makes carbon-deuterium bonds more resistant to oxidative degradation, thus, a deuteration approach has been utilized in medicinal chemistry to enhance drug property, and at least one deuterated drug has been licensed with others in development. Therefore, we generated three deuterated variants of GC376 by replacing hydrogen with deuterium at the metabolic soft spots encompassed in the X moiety (aromatic ring and benzylic carbon) and evaluated their activity in the enzyme and the cell-based assays. All three X moiety-deuterated variants (aldehydes and their bisulfite adducts) showed modestly increased potency compared to GC376, which was more apparent in the cell-based assays than in the enzyme assay (Table 2).

Crystal structures of deuterated GC376 (compound 2) and the 3CLpro of SARS-CoV-2 revealed that deuteration did not alter the interactions between GC376 and 3CLpro which are reported by other groups. It may be speculated that the enhanced activity of the deuterated compounds can be attributed to tighter binding to the target, which was observed with other deuterated compounds or improved physicochemical properties of the compound. However, further study is needed to understand the mechanism. Substitution of the aldehyde warhead in compound 1 with an α-ketoamide (compound 5) significantly decreased potency, which confirms earlier findings by us that ketoamide is less suitable for coronavirus 3CLpro inhibition. Employing an OCOmethyl or n-pentyl ester derivative of bisulfite adducts to produce prodrug variants (compounds 3, 4, 8 and 11) led to reduced potency in the enzyme assay, which may be due to inefficient conversion to the active compound in the enzyme assay.

In the K18-hACE2 mice infected with SARS-CoV-2, once daily administration of compound 2 starting at 24 hr post infection to mice infected with 50% or 100% lethality resulted in significant reductions in body weight loss and nearly complete survival of K18 mice. The kinetics of virus clearance was enhanced, and lung pathological changes were diminished by drug treatment.

In summary, we show that deuterated variants of GC376 are potent inhibitors of SARS-CoV-2 replication and significantly enhance survival of infected mice. Importantly, this approach has wide applicability, and strategic deuteration can be extended to multiple FDA-approved drugs currently under investigation as COVID-19 therapeutics with potential improvement in clinical outcomes.

Materials and Methods

Study Design. The primary objective of this study was to evaluate the antiviral activity of deuterated variants of GC376, a protease inhibitor that is currently under investigation for the treatment of feline infectious peritonitis and COVID-19, against SARS-CoV-2 in vitro, as well as antiviral efficacy in a fatal mouse model of SARS-CoV-2 infection.

Biocontainment and biosafety of coronaviruses. All studies with SARS-CoV-2 were performed in biosafety level 3 facilities at the University of Iowa. All experiments were conducted under protocols approved by the Institutional Biosafety Committee at the University of Iowa according to guidelines set by the Biosafety in Microbiological and Biomedical Laboratories, the U.S. Department of Health and Human Services, the U.S. Public Health Service, the U.S. Centers for Disease Control and Prevention, and the National Institutes of Health.

Synthesis of deuterated variants of GC376 3CLpro inhibitors. Compounds 1-11 were readily synthesized using a reaction sequence (FIG. 4) using alcohol inputs as listed in Table 2. Briefly, the deuterated alcohol inputs were reacted with (L) leucine isocyanate methyl ester to yield the corresponding dipeptidyl methyl esters which were then hydrolyzed to the corresponding acids with lithium hydroxide in aqueous tetrahydrofuran. Subsequent carbonyl diimidazole (CDI)-mediated coupling of the acids to glutamine surrogate methyl ester furnished the dipeptidyl methyl esters. Lithium borohydride reduction yielded the alcohols which were then oxidized to the corresponding aldehydes with Dess-Martin periodinane reagent. The bisulfite adducts were generated by treatment with sodium bisulfite in aqueous ethanol and ethyl acetate. An alternative convergent synthesis of compounds 1-11 entailed the activation of a deuterated alcohol with disuccinimidyl carbonate followed by sequential coupling with a dipeptidyl amino alcohol and oxidation with Dess-Martin periodinane. The synthesis of α-ketoamide compound 5 was accomplished by reacting the Z-protected dipeptidyl aldehyde with benzyl isonitrile to yield the α-hydroxyketoamide followed by Dess-Martin oxidation. Prodrug compounds 3, 4, 8 and 11 were synthesized by refluxing the aldehyde bisulfite adduct with acetic anhydride or n-hexanoic anhydride.

Compound 1

Phenylmethyl-d2 ((S)-4-methyl-1-oxo-1-(((S)-1-oxo-3-((S)-2-oxopyrrolidin-3-yl)propan-2-yl)amino)pentan-2-yl)carbamate (1). Yield (57%), mp 45-48° C. $^1$H NMR (400 MHz, CDCl$_3$): δ 9.48 (s, 1H), 8.32 (d, J=5.9 Hz, 1H), 7.38-7.28 (m, 5H), 6.18 (s, 1H), 5.44 (d, J=8.6 Hz, 1H), 4.40-4.29 (m, 2H), 3.36-3.29 (m, 2H), 2.52-2.22 (m, 2H), 2.01-1.79 (m, 2H), 1.79-1.64 (m, 3H), 1.60-1.50 (m, 1H), 0.97 (d, J=5.7 Hz, 6H). HRMS m/z: [M+H]$^+$ Calculated for C$_{21}$H$_{28}$D$_2$N$_3$O$_5$: 406.2311. Found: 406.2314; m/z: [M+Na]$^+$ Calculated for C$_{21}$H$_{28}$D$_2$N$_3$NaO$_5$: 428.2131. Found: 428.2136.

Compound 2

Sodium (2S)-1-hydroxy-2-((S)-4-methyl-2-(((phenylmethoxy-d2)carbonyl)amino)pentan-amido)-3-((S)-2-oxopyrrolidin-3-yl)propane-1-sulfonate (2). Yield (69%), mp 118-120° C. $^1$H NMR (400 MHz, DMSO-d$_6$) δ 7.65 (d, J=9.2 Hz, 1H), 7.59 (d, J=9.3 Hz, 1H), 7.49 (d, J=8.4 Hz, 1H), 7.33-7.27 (m, 5H), 5.49 (d, J=6.2 Hz, 1H), 5.33 (d, J=6.0 Hz, 1H), 4.27-4.19 (m, 1H), 3.88-3.83 (m, 1H), 3.18j-2.96 (m, 2H), 2.21-1.89 (m, 2H), 1.67-1.50 (m, 2H), 1.50-1.38 (m, 4H), 0.83 (d, J=2.9 Hz, 6H). HRMS m/z: [M+H]$^+$ Calculated for C$_{21}$H$_{29}$D$_2$N$_3$NaO$_8$S: 510.1855, Found: 510.1838.

Compound 3

Sodium (5S,8S)-5-isobutyl-3,6,11-trioxo-8-(((S)-2-oxopyrrolidin-3-yl)methyl)-1-phenyl-2,10-dioxa-4,7-diazadodecane-9-sulfonate-1,1-d2 (3). Yield (72%), mp 110-113° C. $^1$H NMR (400 MHz, DMSO-d$_6$) δ 7.70-7.62 (m, 2H), 7.49 (s, 1H), 7.41-7.30 (m, 5H), 5.10 (d, J=8.9 Hz, 1H), 4.41-3.80 (m, 2H), 3.18-3.03 (m, 2H), 2.30-1.82 (m, 2H), 1.77 (s, 3H), 1.69-1.32 (m, 6H), 0.83 (d, J=5.9 Hz, 6H). HRMS m/z: [M+H]$^+$ Calculated for C$_{23}$H$_{31}$D$_2$N$_3$NaO$_9$S: 552.1960. Found: 552.1953, m/z: [M+Na]$^+$ Calculated for C$_{23}$H$_{30}$D$_2$N$_3$Na$_2$O$_9$S: 574.1780, Found: 574.1777 m/z: [M]$^-$ Calculated for C$_{23}$H$_{30}$D$_2$N$_3$O$_9$S: 528.1984, Found: 528.1993.

Compound 4

Sodium (5S,8S)-5-isobutyl-3,6,11-trioxo-8-(((S)-2-oxopyrrolidin-3-yl)methyl)-1-phenyl-2,10-dioxa-4,7-diazahexadecane-9-sulfonate-1,1-d2 (4). Yield (64%), mp 100-104° C. $^1$H NMR (400 MHz, DMSO-d$_6$) δ 7.68 (d, J=10.4 Hz, 1H), 7.51 (d, J=8.2 Hz, 1H), 7.47 (s, 1H), 7.42-7.23 (m, 5H), 5.11 (d, J=8.7 Hz, 1H), 4.34-4.00 (m, 1H), 4.00-3.83 (m, 1H), 3.21-2.91 (m, 2H), 2.41-1.99 (m, 4H), 1.99-1.74 (m, 1H), 1.74-1.33 (m, 7H), 1.35-1.16 (m, 4H), 0.86 (d, J=12.6 Hz, 9H). HRMS m/z: [M+H]$^+$ Calculated for C$_{27}$H$_{39}$D$_2$N$_3$NaO$_9$S 608.2586. Found: 608.2581; m/z: [M+Na]$^+$ Calculated for C$_{27}$H$_{38}$D$_2$N$_3$Na$_2$O$_9$S: 630.2406, Found: 630.2404; m/z: [M]$^-$ Calculated for C$_{27}$H$_{38}$D$_2$N$_3$O$_9$S: 584.2610, Found: 584.2623.

Compound 5

Phenylmethyl-d2 ((S)-1-(((S)-4-(benzylamino)-3,4-dioxo-1-((S)-2-oxopyrrolidin-3-yl) butan-2-yl)amino)-4-methyl-1-oxopentan-2-yl)carbamate (5). Yield (40%), mp 124-128° C. $^1$H NMR (400 MHz, CDCl$_3$) δ8.43 (d, 7-6.1 Hz, 1H), 7.49 (t, J=6.2 Hz, 1H), 7.37-7.19 (m, 10H), 6.89 (s, 1H), 5.73 (d, 7=8.7 Hz, 1H), 4.48-4.42 (m, 2H), 4.42-4.17 (m, 2H), 3.32-3.09 (m, 2H), 2.57-2.43 (m, 1H), 2.43-2.29 (m, 1H), 2.29-2.12 (m, 1H), 1.96-1.81 (m, 1H), 1.81-1.56 (m, 3H), 1.56-1.45 (m, 1H), 0.93 (d, 7=6.5 Hz, 6H). HRMS m/z: [M+H]$^+$ Calculated for C$_{29}$H$_{35}$D$_2$N$_4$O$_6$: 539.2838, Found: 539.2842; m/z: [M+Na]$^+$ Calculated for C$_{29}$H$_{34}$D$_2$N$_4$NaO$_6$: 561.2658, Found: 561.2661.

Compound 6

(Phenyl-d5)methyl ((S)-4-methyl-1-oxo-1-(((S)-1-oxo-3-((S)-2-oxopyrrolidin-3-yl) propan-2-yl)amino)pentan-2-yl) carbamate (6). Yield (62%), mp 40-43° C. $^1$H NMR (400 MHz, DMSO-d$_6$) δ 9.40 (s, 1H), 8.48 (d, 7=7.6 Hz, 1H), 7.49 (s, 1H), 7.38 (d, 7=8.3 Hz, 1H), 5.03-5.03 (m, 2H), 4.24-4.13 (m, 1H), 4.09-3.99 (m, 1H), 3.19-2.92 (m, 2H), 2.37-1.95 (m, 2H), 1.89-1.75 (m, 1H), 1.71-1.48 (m, 2H), 1.47-1.33 (m, 3H), 0.86 (d, 7=2.1 Hz, 6H). HRMS m/z: [M+H]$^+$ Calculated for C$_{21}$H$_{25}$D$_5$N$_3$O$_5$:409.2499, Found: 409.2528, m/z: [M+Na]$^+$ Calculated for C$_{21}$H$_{24}$D$_5$N$_3$NaO$_5$: 431.2319, Found: 431.2348.

Compound 7

Sodium (2S)-1-hydroxy-2-((S)-4-methyl-2-((((phenyl-d5)methoxy)carbonyl)amino) pentanamido)-3-((S)-2-oxopyrrolidin-3-yl)propane-1-sulfonate (7). Yield (68%), mp 125-128° C. $^1$H NMR (400 MHz, DMSO-d$_6$) δ 7.64 (d, 7=9.1 Hz, 1H), 7.59 (d, 7=9.3 Hz, 1H), 7.49 (d, 7=8.1 Hz, 1H), 5.44 (d, 7=6.3 Hz, 2H), 5.29 (d, 7=6.0 Hz, 1H), 5.05-4.98 (m, 2H), 4.03-3.87 (m, 2H), 3.17-2.95 (m, 2H), 2.24-2.02 (m, 2H), 1.83-1.50 (m, 3H), 1.49-1.37 (m, 2H), 0.84 (d, 7=3.0 Hz, 6H). HRMS m/z: [M+H]$^+$ Calculated for C$_{21}$H$_{26}$D$_5$N$_3$NaO$_8$S: 513.2043, Found: 513.2054, m/z: [M+Na]$^+$ Calculated for C$_{21}$H$_{25}$D$_5$N$_3$Na$_2$O$_8$S: 535.1863, Found: 535.1904.

Compound 8

Sodium (5S,8S)-5-isobutyl-3,6,11-trioxo-8-(((S)-2-oxopyrrolidin-3-yl)methyl)-1-(phenyl-d5)-2,10-dioxa-4,7-diazahexadecane-9-sulfonate (8). Yield (67%), mp 110-112° C. $^1$H NMR (400 MHz, DMSO-d$_6$) δ 7.87 (d, J=9.3 Hz, 1H), 7.68 (d, J=9.9 Hz, 1H), 7.50 (d, J=9.5 Hz, 1H), 5.11 (d, J=8.9 Hz, 1H), 5.04-5.01 (m, 2H), 4.38-4.04 (m, 1H), 4.04-3.80 (m, 1H), 3.21-2.89 (m, 2H), 2.37-2.06 (m, 2H), 2.01 (t, J=7.4 Hz, 3H), 1.98-1.67 (m, OH), 1.67-1.55 (m, 4H), 1.45 (p, J=7.4 Hz, 2H), 1.39-1.33 (m, 1H), 1.32-1.16 (m, 4H), 0.93-0.76 (m, 9H). HRMS m/z: [M+H]$^+$ Calculated for C$_{27}$H$_{36}$D$_5$N$_3$NaO$_9$S: 611.2775, Found: 611.2816.

Compound 9

(Phenyl-d5)methyl-d2 ((S)-4-methyl-1-oxo-1-(((S)-1-oxo-3-((S)-2-oxopyrrolidin-3-yl)propan-2-yl)amino)pentan-2-yl)carbamate (9). Yield (70%), mp 45-48° C. $^1$H NMR (400 MHz, DMSO-d$_6$) δ 9.40 (s, 1H), 8.48 (d, J=7.6 Hz, 1H), 7.63 (s, 1H), 7.47 (d, J=8.3 Hz, 1H), 4.23-4.17 (m, 1H), 4.12-4.03 (m, 1H), 3.23-2.95 (m, 2H), 2.37-2.03 (m, 3H), 1.93-1.81 (m, 1H), 1.74-1.56 (m, 3H), 1.56-1.36 (m, 3H), 0.87 (d, J=6.6 Hz, 6H). HRMS m/z: [M+H]$^+$ Calculated for C$_{21}$H$_{23}$D$_7$N$_3$O$_5$: 411.2625, Found: 411.2622, m/z: [M+Na]$^+$ Calculated for C$_{21}$H$_{22}$D$_7$N$_3$NaO$_5$. 433.2445, Found: 433.2440.

Compound 10

Sodium(2S)-1-hydroxy-2-((S)-4-methyl-2-((((phenyl-d5)methoxy-d2)carbonyl)amino) pentanamido)-3-((S)-2-oxopyrrolidin-3-yl)propane-1-sulfonate (10). Yield (82%), mp 120-122° C. $^1$H NMR (400 MHz, DMSO-do) δ 7.66 (d, J=9.1 Hz, 0H), 7.60 (d, J=9.5 Hz, 1H), 7.50 (s, 1H), 5.51 (d, 0.7=6.2 Hz, 1H), 5.34 (d, J=6.0 Hz, 0H), 4.06-3.97 (m, 1H), 3.97-3.90 (m, 1H), 3.15-3.07 (m, 2H), 2.21-2.01 (m, 3H), 2.01-1.71 (m, 1H), 1.71-1.49 (m, 4H), 1.49-1.31 (m, 2H), 0.87 (d, J=4.7 Hz, 6H). HRMS m/z: [M+H]$^+$ Calculated for C$_{21}$H$_{24}$D$_7$N$_3$NaO$_8$S: 515.2169, Found: 515.2152.

Compound 11

Sodium (5S,8S)-5-isobutyl-3,6,11-trioxo-8-(((S)-2-oxopyrrolidin-3-yl)methyl)-1-(phenyl-d5)-2,10-dioxa-4,7-diazahexadecane-9-sulfonate-1,1-d2 (11). Yield (44%), mp 100-105° C. $^1$H NMR (400 MHz, DMSO-d$_6$) δ 7.64 (d, J=8.7 Hz, 1H), 7.48 (s, 1H), 7.35 (d, J=8.0 Hz, 1H), 5.13 (d, 7=8 8 Hz, 1H), 4.16-4.03 (m, 1H), 4.05-3.87 (m, 1H), 3.21-2.87 (m, 2H), 2.40-1.99 (m, 4H), 1.99-1.76 (m, 1H), 1.76-1.34 (m, 7H), 1.34-1.18 (m, 4H), 0.96-0.69 (m, 9H). HRMS m/z: [M+H]$^+$ Calculated for $C_{27}H_{34}D_7N_3NaO_9S$: 613.2900, Found: 613.2899, m/z: [M]$^-$ Calculated for $C_{27}H_{33}D_7N_3O_9S$: 589.2924, Found: 589.2940.

Fluorescence resonance energy transfer (FRET) enzyme assay. The cloning, expression, and purification of the 3CLpro of SARS-CoV-2 were conducted by a standard method. The codon-optimized cDNA of full length 3CLpro of SARS-CoV-2 (GenBank number MN908947.3) fused with sequences encoding 6 histidine at the N-terminal was synthesized by Integrated DNA Technologies (Coralville, IA). The synthesized gene was subcloned into the pET-28a (+) vector. The FRET enzyme assays were conducted. Briefly, stock solutions of compounds 1-11 were prepared in DMSO and diluted in assay buffer, which was comprised of 20 mM HEPES buffer, pH 8, containing NaCl (200 mM), EDTA (0.4 mM), glycerol (60%), and 6 mM dithiothreitol (DTT). The SARS-CoV-2 3CL protease was mixed with serial dilutions of each compound or with DMSO in 25 µL of assay buffer and incubated at room temperature for 1 hr (SARS-CoV-2 and SARS-CoV), followed by the addition of 25 µL of assay buffer containing substrate (FAM-SAVLQ/SG-QXL® 520, AnaSpec, Fremont, CA). The substrate was derived from the cleavage sites on the viral polyproteins of SARS-CoV. Fluorescence readings were obtained using an excitation wavelength of 480 nm and an emission wavelength of 520 nm on a fluorescence microplate reader (FLx800; Biotec, Winoosk, VT) at 1 hr following the addition of the substrate. Relative fluorescence units (RFU) were determined by subtracting background values (substrate-containing well without protease) from the raw fluorescence values. The dose-dependent FRET inhibition curves were fitted with a variable slope using GraphPad Prism software (GraphPad, La Jolla, CA) to determine the 50% inhibitory concentration ($IC_{50}$) values of the compounds, which are listed in Table 2.

Cell-based assay for antiviral activity. Compounds 1, 2, 6 and 7 were investigated for their antiviral activity against the replication of SARS-CoV-2. Briefly, confluent Vero E6 cells were inoculated with SARS-CoV-2 at 50-100 plaque forming units/well, and medium containing various concentrations of each compound and agar was applied to the cells. After 48-72 hr, plaques in each well were counted. The 50% effective concentration ($EC_{50}$) values were determined by GraphPad Prism software using a variable slope (GraphPad, La Jolla, CA).

Nonspecific cytotoxic effects. The 50% cytotoxic concentrations ($CC_{50}$) of compounds 1-11 were determined in Vero E6 and CRFK cells. Confluent cells grown in 96-well plates were incubated with various concentrations (1 to 100 µM) of each compound for 72 hr. Cell cytotoxicity was measured by a CytoTox 96 nonradioactive cytotoxicity assay kit (Promega, Madison, WI), and the $CC_{50}$ values were calculated using a variable slope by GraphPad Prism software (Table 2).

X-ray crystallographic studies: protein purification, crystallization, and data collection. Purified SARS-CoV 3CLpro and SARS-CoV-2 3CLpro were concentrated to 22.0 mg/mL (0.64 mM) and 9.6 mg/mL (0.28 mM), respectively, in 100 mM NaCl, 20 mM Tris pH 8.0 for crystallization screening. All crystallization experiments were set up using an NT8 drop-setting robot (Formulatrix Inc.) and UVXPO MRC (Molecular Dimensions) sitting drop vapor diffusion plates at 18° C. 100 nL of protein and 100 nL crystallization solution were dispensed and equilibrated against 50 µL of the latter. Stock solutions of compounds 2 and 5 (100 mM) were prepared in DMSO and the 3CLpro:inhibitor complexes were prepared by adding 2 mM ligand to the proteases and incubating on ice for 1 hr. Crystals were obtained in 1-2 days from the following conditions. SARS-CoV 3CLpro complex with compound 2: Index HT screen (Hampton Research) condition H4 (30% (w/v) PEG 3350, 200 mM ammonium citrate pH 7.0). SARS-CoV 3CLpro complex with compound 5: Berkeley screen (Rigaku Reagents) condition B1 (30% (w/v) PEG 3350, 100 mM Tris pH 8.5, 400 mM sodium chloride). SARS-CoV-2 3CLpro complex with compound 2: Index HT screen (Rigaku Reagents) condition G8 (25% (w/v) PEG 3350, 100 mM Hepes pH 7.5, 200 mM ammonium acetate). SARS-CoV-2 3CLpro complex with compound 5: Index HT condition D11 (28% PEG 2000 MME, 100 mM Bis-Tris pH 6.5). Samples were transferred to a fresh drop composed of 80% crystallization solution and 20% (v/v) PEG 200 and stored in liquid nitrogen. All X-ray diffraction data were collected using a Dectris Eiger2 X 9M pixel array detector at the Advanced Photon Source IMCA-CAT beamline 17-ID except for the data for the SARS-CoV-2 3CLpro complex with compound 5 which were collected at the National Synchrotron Light Source II (NSLS-II) AMX beamline 17-ID-1.

Structure solution and refinement. Intensities were integrated using XDS via Autoproc and the Laue class analysis and data scaling were performed with Aimless. Structure solution was conducted by molecular replacement with Phaser using previously determined structures of SARS-CoV 3CLpro (PDB 6W2A) and SARS-CoV-2 3CLpro (PDB 6XMK) as the search models. Structure refinement and manual model building were conducted with Phenix and Coot, respectively. Disordered side chains were truncated to the point for which electron density could be observed. Structure validation was conducted with Molprobity, and figures were prepared using the CCP4MG package. Superpositions were performed using GESAMT. Crystallographic data are provided in Table 3.

TABLE 3

Crystallographic data for SARS-CoV and SARS-CoV-2 3CLpro structures.

|  | SARS-CoV-2 compound 2 | SARS-CoV-2 compound 5 | SARS-CoV compound 2 | SARS-CoV compound 5 |
|---|---|---|---|---|
| Data Collection |  |  |  |  |
| Unit-cell parameters (Å, °) | a = 55.12 | a = 55.25 | a = 107.88 | a = 55.03 |
|  | b = 98.83 | b = 98.53 | b = 45.19 | b = 98.97 |
|  | c = 58.95 | c = 58.96 | c = 53.52 | c = 59.67 |
|  | β = 107.8 | β = 108.0 |  | b = 108.0 |
| Space group | P2$_1$ | P2$_1$ | P2$_1$2$_1$2 | P2$_1$ |
| Resolution (Å)[1] | 49.42-1.90 | 46.36-1.65 | 47.94-1.85 | 49.49-1.70 |
|  | (1.94-1.90) | (1.68-1.65) | (1.89-1.85) | (1.73-1.70) |

TABLE 3-continued

Crystallographic data for SARS-CoV and SARS-CoV-2 3CLpro structures.

|  | SARS-CoV-2 compound 2 | SARS-CoV-2 compound 5 | SARS-CoV compound 2 | SARS-CoV compound 5 |
|---|---|---|---|---|
| Wavelength (Å) | 1.0000 | 0.9201 | 1.000 | 1.0000 |
| Temperature (K) | 100 | 100 | 100 | 100 |
| Observed reflections | 163,367 | 247,132 | 187,771 | 283,870 |
| Unique reflections | 46,687 | 70,687 | 23,106 | 66,700 |
| $<I/\sigma(I)>^1$ | 8.8 (2.0) | 10.7 (1.6) | 13.7 (1.9) | 10.5 (2.0) |
| Completeness (%)[1] | 98.6 (100) | 98.3 (96.9) | 100 (100) | 99.9 (100) |
| Multiplicity[1] | 3.5 (3.6) | 3.5 (3.5) | 8.1 (8.4) | 4.3 (4.4) |
| $R_{merge}$ (%)[1,2] | 7.4 (56.5) | 6.1 (79.0) | 7.6 (120.5) | 6.7 (75.1) |
| $R_{meas}$ (%)[1,4] | 8.7 (66.4) | 7.2 (93.3) | 8.1 (128.4) | 7.7 (85.5) |
| $R_{pim}$ (%)[1,4] | 4.6 (34.6) | 3.8 (49.1) | 2.9 (43.8) | 3.7 (40.3) |
| $CC_{1/2}$[1,5] | 0.996 (0.845) | 0.998 (0.676) | 0.998 (0.679) | 0.997 (0.822) |
| Refinement |  |  |  |  |
| Resolution (Å)[1] | 37.09-1.90 | 46.36-1.65 | 34.64-1.85 | 46.27-1.70 |
| Reflections (working/test)[1] | 44,269/2,348 | 67,180/3,463 | 21,933/1,130 | 63,330/3,304 |
| $R_{factor}$ / $R_{free}$ (%)[1,3] | 18.1/23.0 | 18.1/22.5 | 19.2/24.0 | 17.4/21.0 |
| No. of atoms (Protein/Ligand/Water) | 4,483/58/197 | 4,493/78/337 | 2,203/58/127 | 4,510/72/298 |
| Model Quality |  |  |  |  |
| R.m.s deviations |  |  |  |  |
| Bond lengths (Å) | 0.011 | 0.011 | 0.009 | 0.010 |
| Bond angles (°) | 1.069 | 1.037 | 1.000 | 1.053 |
| Mean B-factor (Å$^2$) |  |  |  |  |
| All Atoms | 37.4 | 29.6 | 40.1 | 32.5 |
| Protein | 37.3 | 29.0 | 40.1 | 32.0 |
| Ligand | 39.4 | 34.3 | 34.2 | 33.7 |
| Water | 40.1 | 36.0 | 42.5 | 38.4 |
| Coordinate error (maximum likelihood) (Å) | 0.24 | 0.21 | 0.24 | 0.18 |
| Ramachandran Plot |  |  |  |  |
| Most favored (%) | 96.6 | 98.1 | 94.8 | 98.0 |
| Additionally allowed (%) | 3.4 | 1.9 | 4.5 | 2.0 |

[1] Values in parenthesis are for the highest resolution shell.
[2] Rmerge = Σhk/Σi |Ii(hkl) - <I(hkl)>| / ΣhklΣi Ii(hkl), where Ii(hkl) is the intensity measured for the ith reflection and <I(hkl)> is the average intensity of all reflections with indices hkl.
[3] Rfactor = Σhkl ||Fobs (hkl)| - |Fcalc (hkl)|| / Σhkl |Fobs (hkl)|; Rfree is calculated in an identical manner using 5% of randomly selected reflections that were not included in the refinement.
[4] Rmeas = redundancy-independent (multiplicity-weighted) Rmerge. Rpim = precision-indicating (multiplicity-weighted) Rmerge.
[5] CC1/2 is the correlation coefficient of the mean intensities between two random half-sets of data.

Post-infection treatment in a mouse model of SARS-CoV-2 infection. Compound 2 was examined for efficacy using 7-8-week-old female K18-hACE2 mice infected with SARS-CoV-2. In the first experiment, animals were divided into two groups (N=4 for vehicle or N=5 for compound 2) and were lightly anesthetized with ketamine/xylazine prior to infection with 50 μl of $2 \times 10^3$ pfu SARS-CoV-2 [The 2019n-CoV/USA-WA1/2019 strain of SARS-CoV-2 (accession number. MT985325.1)] via intranasal inoculation. Compound 2 was formulated in 10% ethanol and 90% PEG400 and given to mice from 1 (24 hr post infection) to 10 days post infection (dpi) at 100 mg/kg/day (once per day) via intraperitoneal administration. Control mice received vehicle. Animals were weighed daily and monitored for 15 days. Animals were euthanized when an animal lost 30% of initial weight or at 15 dpi. In the second experiment, mice were divided into two groups (N=4 for vehicle or N=6 for compound 2) and infected with 50 μl of $5 \times 10^3$ pfu SARS-CoV-2 via intranasal inoculation. Compound 2 was given to mice from 1 (24 hr post infection) to 10 dpi at 125 mg/kg/day (once per day) via intraperitoneal administration. The third experiment was conducted simultaneously with the second one to determine virus titers and histopathology in the lungs of mice treated with vehicle or compound 2 (N=3 for virus titration and N=1 or 2 for histopathology for each group at each dpi). Animals were euthanized at 2 or 5 dpi, and lungs and brains were removed aseptically and disassociated with a manual homogenizer in IX PBS. The homogenized lung and brain tissues were briefly centrifuged, and supernatants were removed. Virus titration was conducted in Vero E6 cells against SARS-CoV-2. For histopathology, lungs and brains were fixed with 10% formalin, and hematoxylin and eosin (HE) stained tissues were examined by a veterinary pathologist using the post-examination method of masking. Lung tissues were evaluated for edema (0-4) using distribution-based ordinal scoring: 0—none; 1—<25% of field; 26-50% of field; 51-75% field and >75% of field. Perivascular inflammation was evaluated by severity-based ordinal scoring: 0—none; 1—scant solitary cellular infiltrates that do not form aggregates; 2—Mild infiltrates that form loose cuff (~1 cell thickness) around vessel; 3—infiltrates form a distinct perivascular aggregate ~2-4 cells thick, and 4—large perivascular aggregates (>4 cells thick that extend to compress adjacent tissues.

Statistical analysis. Multiple T-test were used to analyze body weight change and lung virus titers between groups using GraphPad Prism Software version 6 (San Diego, CA). Log-rank (Mantel-Cox) test was used for analysis of survival curves between groups using GraphPad Prism P<0.05 was considered statistically significant.

Example 3

Additional Compounds

Based upon the platform for compound design described above, additional compounds are synthesized using various warhead variants from the aldehydes, bisulfite salt adducts, and/or prodrug forms thereof, with deuterium substitutions within the linkage or in the aromatic group itself.

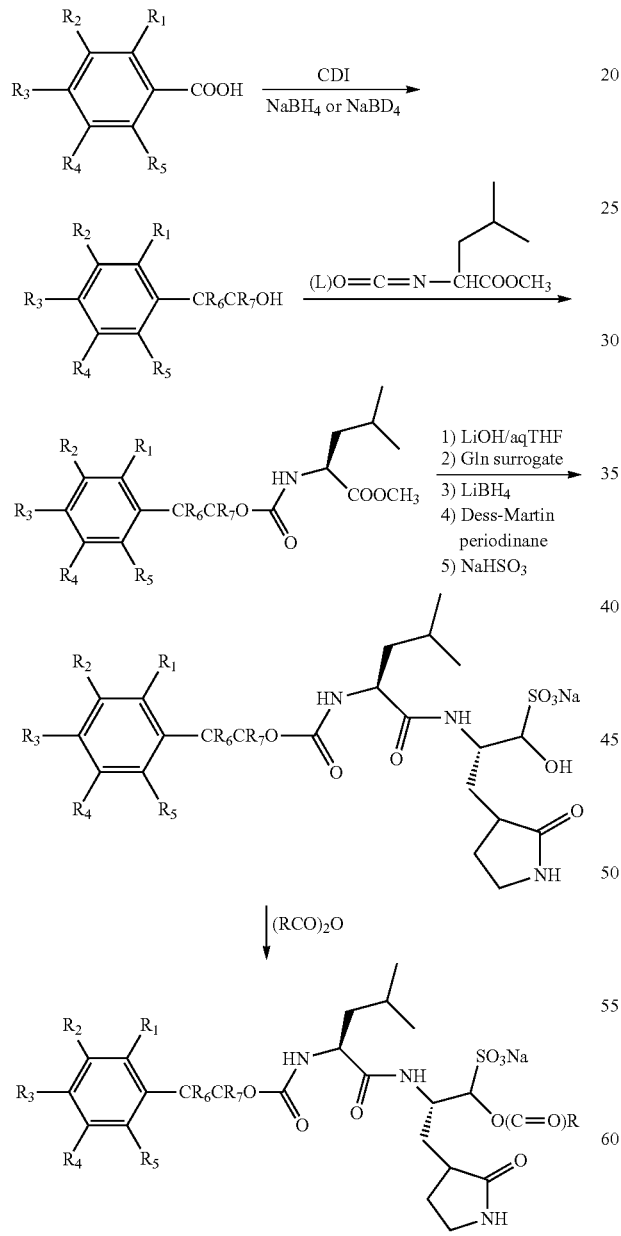

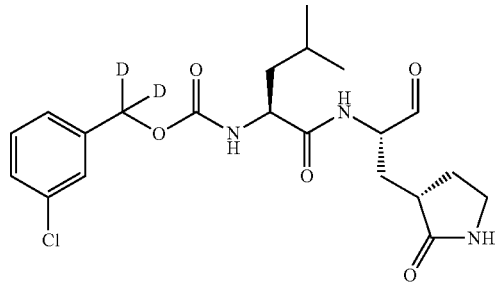

ADR-V-58

Chemical Formula: $C_{21}H_{26}D_2ClN_3O_5$
Molecular Weight: 439.9332

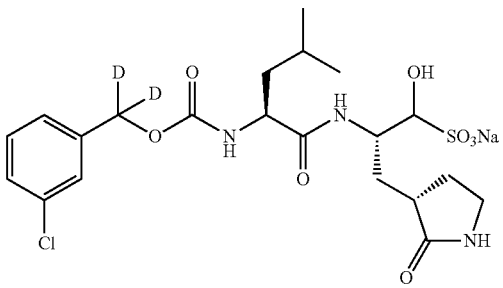

ADR-V-62

Chemical Formula: $C_{21}H_{27}D_2ClN_3NaO_8S$
Molecular Weight: 543.9880

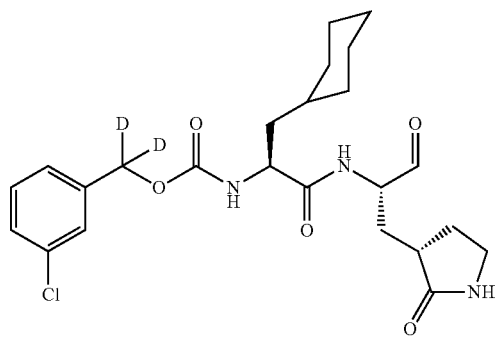

ADR-V-59

Chemical Formula: $C_{24}H_{30}D_2ClN_3O_5$
Molecular Weight: 479.9982

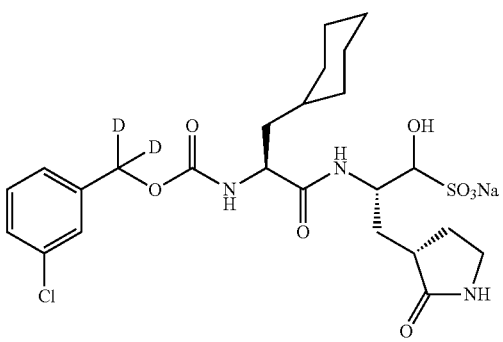

ADR-V-63

Chemical Formula: $C_{24}H_{31}D_2ClN_3NaO_8S$
Molecular Weight: 584.0530

ADR-V-73

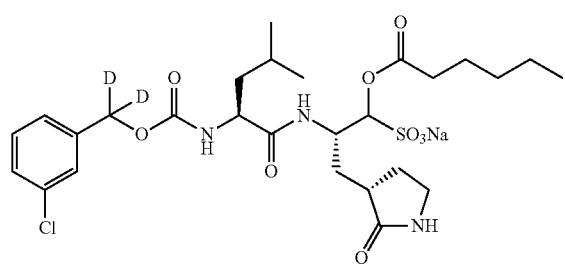

Chemical Formula: $C_{27}H_{37}D_2ClN_3NaO_9S$
Molecular Weight: 642.1330

CSD-II-066

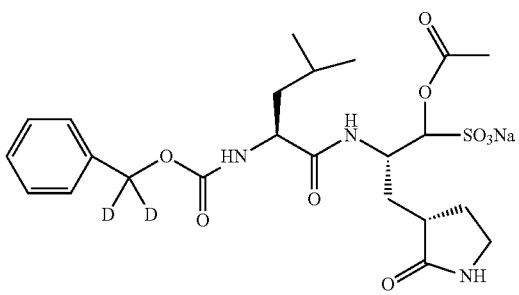

Chemical Formula: $C_{23}H_{30}D_2N_3NaO_9S$
Molecular Weight: 551.58297

ADR-V-74

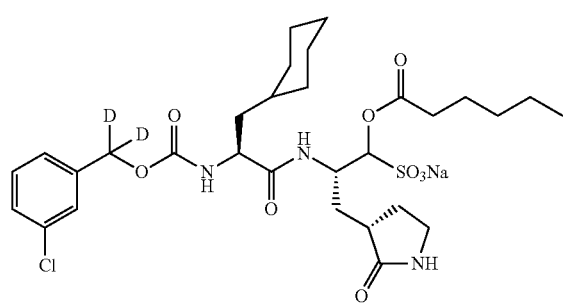

Chemical Formula: $C_{30}H_{41}D_2ClN_3NaO_9S$
Molecular Weight: 682.1980

CSD-II-067

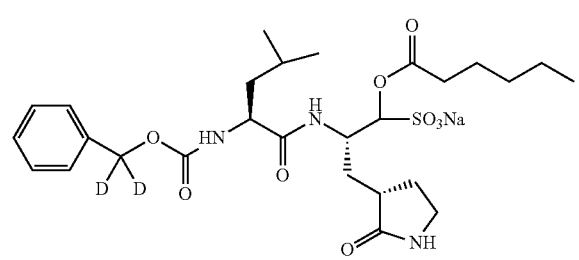

Chemical Formula: $C_{27}H_{38}D_2N_3NaO_9S$
Molecular Weight: 607.69097

CSD-II-054

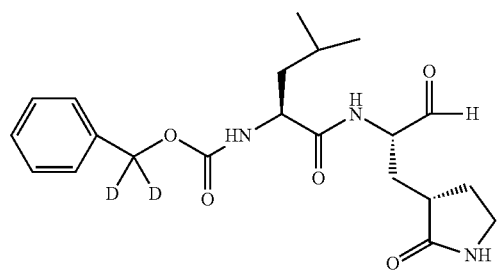

Chemical Formula: $C_{21}H_{27}D_2N_3O_5$
Molecular Weight: 405.49120

CSD-II-069

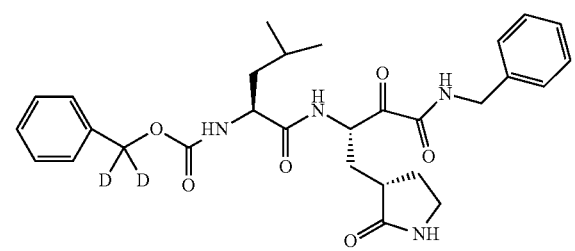

Chemical Formula: $C_{29}H_{34}D_2N_4O_6$
Molecular Weight: 536.64120

CSD-II-055

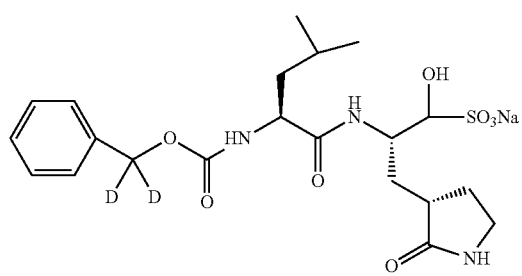

Chemical Formula: $C_{21}H_{28}D_2N_3NaO_8S$
Molecular Weight: 509.54597

CSD-II-070

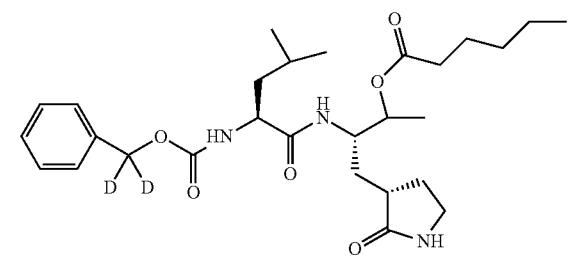

Chemical Formula: $C_{27}H_{33}D_7N_3NaO_9S$
Molecular Weight: 612.72148

These compounds were tested in in vitro assays against SARS-CoV-2, using previously described protocols, and the data is below.

| Reference Name | SARS-CoV-2 3CLpro IC$_{50}$ (μM) |
|---|---|
| ADR-V-58 | 0.33 |
| ADR-V-62 | 0.34 |
| ADR-V-59 | 0.36 |
| ADR-V-63 | 0.35 |
| ADR-V-73 | 1.8 |
| ADR-V-74 | 1.6 |
| CSD-II-054 | 0.18 |
| CSD-II-055 | 0.17 |
| CSD-II-066 | 0.7 |
| CSD-II-067 | 0.8 |
| CSD-II-069 | 1.5 |
| CSD-II-070 | 1.1 |

Figure 4:
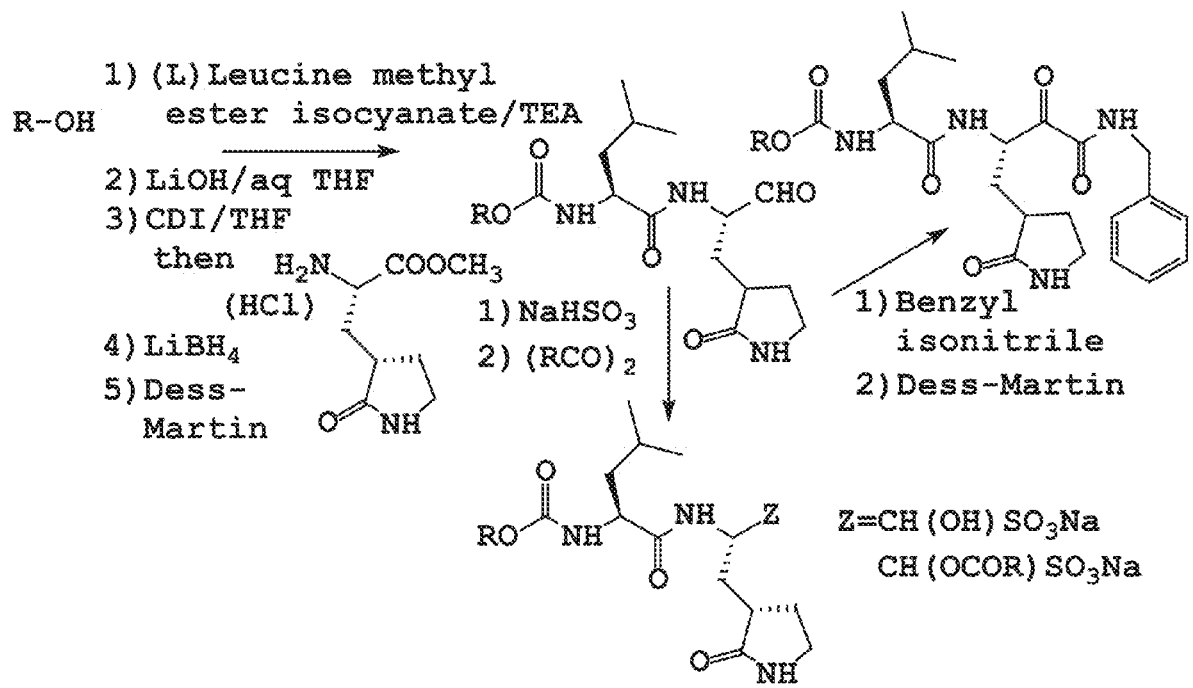
FIG. 4 show the chemical reactions for synthesis of deuterated inhibitors 1-11.

The general reaction scheme in FIG. 4 can also be followed using various alcohol inputs to generate the compounds. Representative collection of additional heterocyclic alcohol inputs in process are shown below, which can be used to synthesize inhibitors having the methylene linkage group to the alcohol input being CH$_2$ or CD$_2$. The compounds exhibit increased aqueous solubility and ability to engage in additional H-bonding interactions.

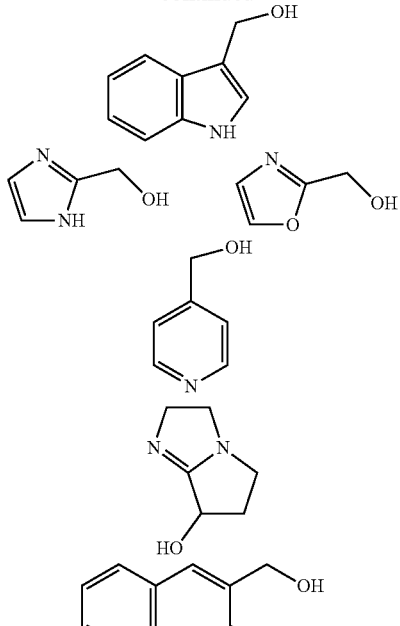

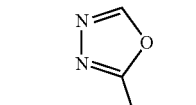

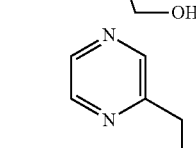

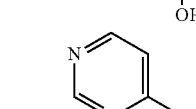

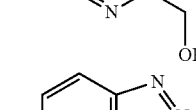

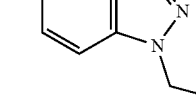

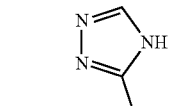

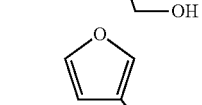

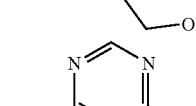

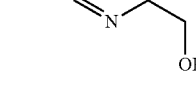

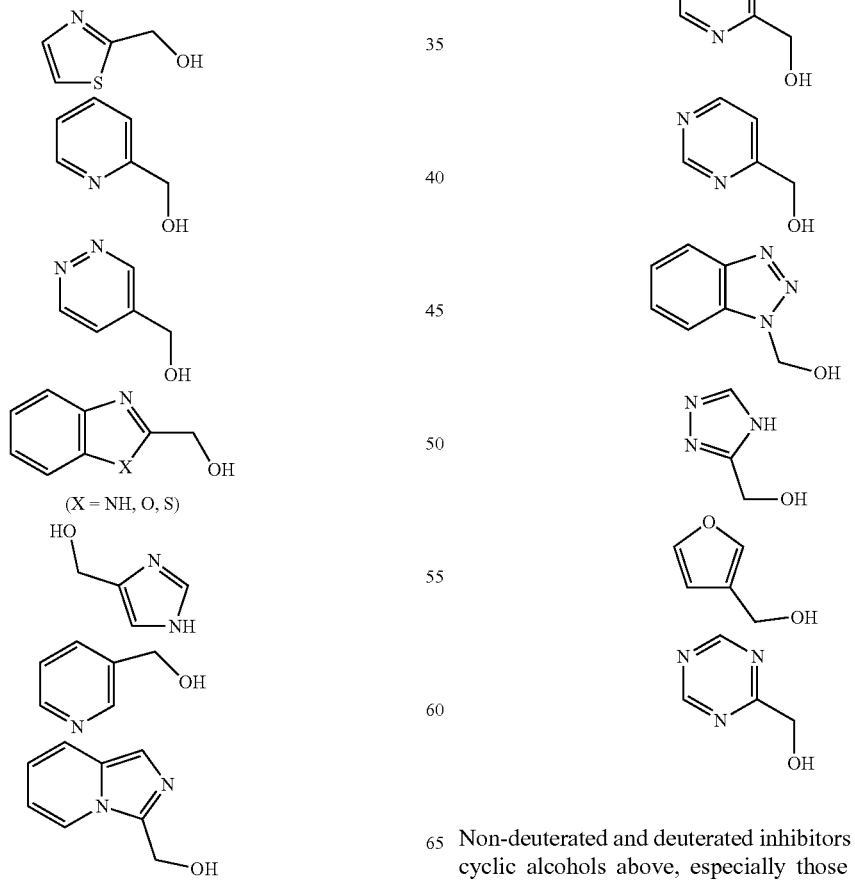

Non-deuterated and deuterated inhibitors made from heterocyclic alcohols above, especially those that incorporate a nitrogen substitution, have augmented pharmacokinetic,

The invention claimed is:

1. A deuterated compound having the structure of formula I, or a prodrug or pharmaceutically-acceptable salt thereof:

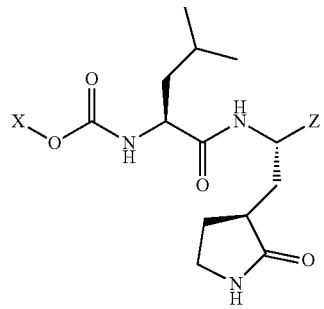

(I)

where:
each X is at least one cyclic moiety directly attached to the oxygen or connected via an alkyl linkage, where at least one of the linkage and/or the cyclic moiety comprises a deuterium substitution; and
Z is selected from the group consisting of aldehydes and bisulfite salts, or the ester or carbamate prodrugs thereof.

2. The compound, salt, or prodrug of claim 1, wherein Z is —CHO, —SO₃Na, —CH(OH)SO₃⁻Na⁺, —(C=O)(C=O)NHbenzyl, or —CH [O(C=O)R_w]SO₃⁻Na⁺, where R_w is an alkyl or arylalkyl.

3. The compound, salt, or prodrug of claim 1, wherein said compound is a prodrug wherein Z comprises an ester or carbamate moiety.

4. The compound, salt, or prodrug of claim 1, wherein X is a substituted or unsubstituted C₃-C₁₀ cycloalkyl, a substituted or unsubstituted 3-7 membered heterocycle having 1-3 ring heteroatoms selected from N, O, and S, or a substituted or unsubstituted C₆₋₁₀ aryl group.

5. The compound, salt, or prodrug of claim 1, wherein said alkyl linkage comprises a branched or unbranched and substituted or unsubstituted C₁-C₆ alkyl linkage.

6. The compound, salt, or prodrug of claim 1, wherein X—O has a structure selected from the group consisting of:

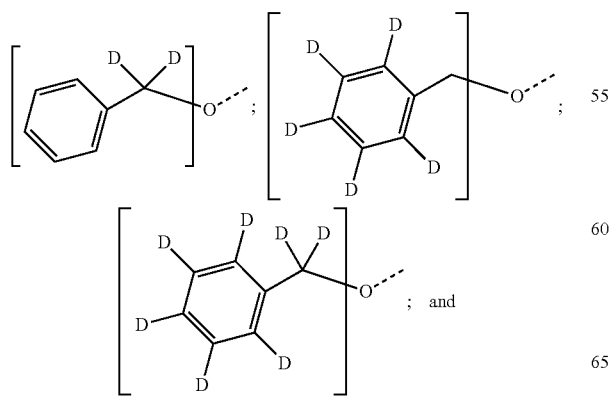

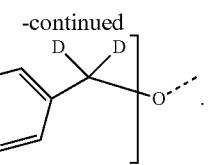

7. The compound, salt, or prodrug of claim 1, having the structure of formula:

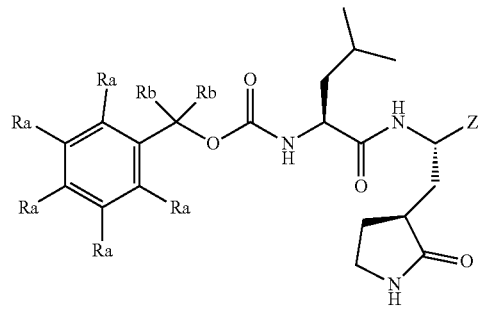

or a prodrug or pharmaceutically-acceptable salt thereof, where each of R_a and R_b, independently, is hydrogen or deuterium, provided that at least one of R_a or R_b is a deuterium atom, optionally wherein at least one R_a is a halogen.

8. The compound, salt, or prodrug of claim 7, wherein at least one R_a is a halogen.

9. The compound, salt, or prodrug of claim 7, wherein each of said R_a and R_b groups are deuterium.

10. The compound, salt, or prodrug of claim 1, said compound comprising a deuterated formula selected from the group consisting of:

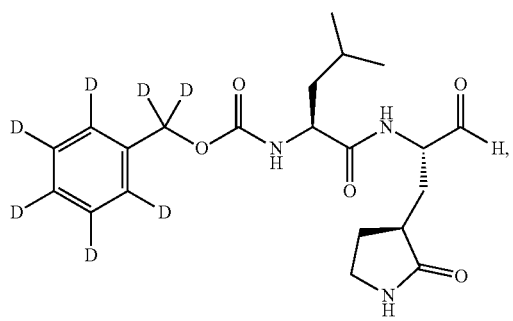

GC1126

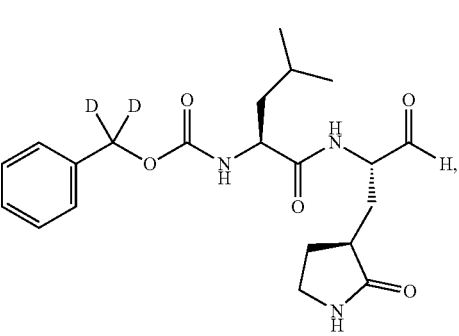

GC1128

-continued

GC1127

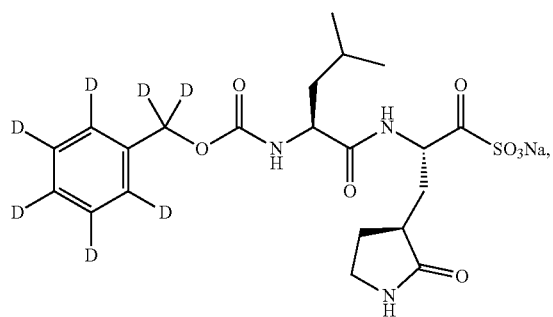

GC1129

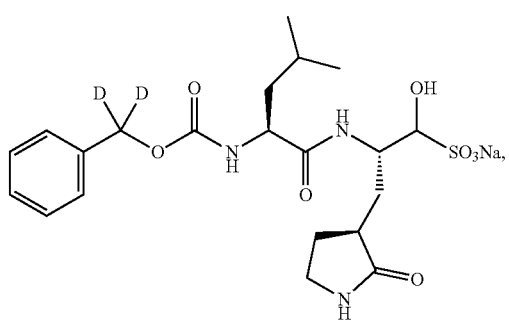

GC1130

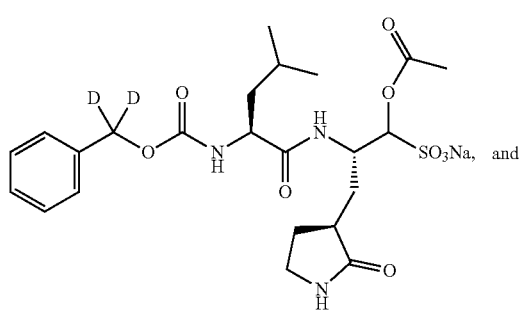

GC1131

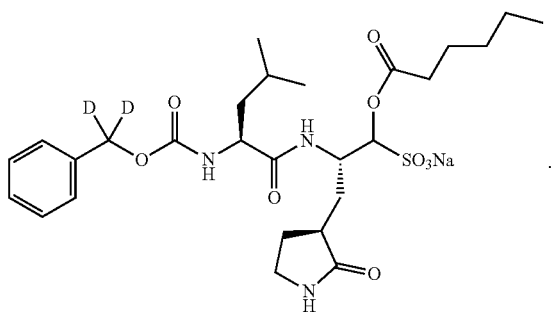

11. The compound, salt or prodrug of claim 1, wherein said compound is a deuterated formula from Table 2:

TABLE 2

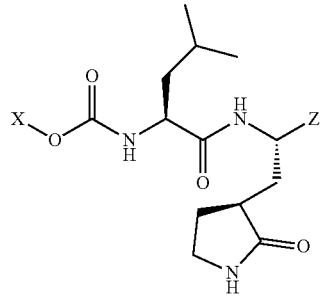

| Compound | Z | X |
|---|---|---|
| 1 | CHO | |
| 2 | CH(OH)SO₃Na | |
| 3 | CH(O(C=O)CH₃)SO₃Na | |
| 4 | CH(O(C=O)n-pentyl)SO₃Na | |
| 5 | (C=O)(C=O)NHbenzyl | |
| 6 | CHO | |
| 7 | CH(OH)SO₃Na | |
| 8 | CH(O(C=O)n-pentyl)SO₃Na | |
| 9 | CHO | |
| 10 | CH(OH)SO₃Na | |
| 11 | CH(O(C=O)n-pentyl)SO₃Na | |

12. A kit comprising a compound, salt, or prodrug according to claim 1; and instructions for administering said compound to a subject in need thereof.

13. The kit of claim 12, wherein the compound, salt, or prodrug is provided in unit dosage form.

14. The kit of claim 12, wherein the compound, salt, or prodrug is provided in a first container, said kit further comprising a carrier in a second container; and instructions for preparing said compound, salt, or prodrug for administration to said subject.

* * * * *